US012788745B2

(12) United States Patent
Dandiker et al.

(10) Patent No.: US 12,788,745 B2
(45) **Date of Patent: *Nov. 10, 2026**

(54) ANTIVIRAL THERAPY WITH IMIQUIMOD AND COCRYSTALS THEREOF

(71) Applicant: CELISTA PHARMACEUTICALS LLC, Edina, MN (US)

(72) Inventors: Yogesh Dandiker, Edina, MN (US); Sita Dandiker, Edina, MN (US)

(73) Assignee: CELISTA PHARMACEUTICALS LLC, Edina, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 18/792,297

(22) Filed: Aug. 1, 2024

(65) Prior Publication Data

US 2024/0390342 A1 Nov. 28, 2024

Related U.S. Application Data

(63) Continuation of application No. 18/002,217, filed as application No. PCT/US2021/038681 on Jun. 23, 2021, now Pat. No. 12,076,313.

(60) Provisional application No. 63/042,704, filed on Jun. 23, 2020.

(51) Int. Cl.

*A61K 31/437* (2006.01)
*A61K 31/192* (2006.01)
*A61K 47/12* (2006.01)
*A61P 37/04* (2006.01)

(52) U.S. Cl.

CPC .......... *A61K 31/437* (2013.01); *A61K 31/192* (2013.01); *A61K 47/12* (2013.01); *A61P 37/04* (2018.01)

(58) Field of Classification Search

None

See application file for complete search history.

(56) References Cited

U.S. PATENT DOCUMENTS

| | | | | |
|---|---|---|---|---|
| 2009/0182004 | A1* | 7/2009 | Winckle | A61K 47/38 514/293 |
| 2011/0178116 | A1 | 7/2011 | Mandrea | |
| 2014/0228451 | A1 | 8/2014 | Roszell et al. | |
| 2016/0331743 | A1 | 11/2016 | Holldack et al. | |
| 2017/0266297 | A1 | 9/2017 | Leoni et al. | |
| 2023/0227448 | A1 | 7/2023 | Dandiker | |

OTHER PUBLICATIONS

Guedes et al., "Imiquimod/beta-Cyclodextrin Inclusion Complex: Experimental and Theoretical Studies," Journal of Brazilian Chemistry Society 31 (8):1732-1745. (Year: 2020).*

Avcilar et al., "Could imiquimod (Aldara 5% cream) or other TLR7 agonists be used in the treatment of COVID-19?" Medical Hypothesis 144:1-3 (2020).

Dockrell et al., "Imiquimod and resiquimod as novel immunomodulators," Journal of Antimicrobial Chemotherapy 48(6):751-755 (2001).

Guedes et al., "Imiquimod/beta-Cyclodextrin Inclusion Complex: Experimental and Theoretical Studies," Journal of Brazilian Chemistry Society 31(8):1732-1745 (2020).

Gunning et al., "Postural Orthostatic Tachycardia Syndrome Is Associated With Elevated G-Protein Coupled Receptor Autoantibodies," Journal of the American Heart Association, 8(18):e013602 (2019).

Poulas et al., "Activation of TLR7 and Innate Immunity as an Efficient Method Against COVID-19 Pandemic: Imiquimod as a Potential Therapy," Frontiers in Immunology 11(1373):1-2 (2020).

The International Search Report and Written Opinion mailed Oct. 1, 2021 in International Application No. PCT/US2021/038681.

The International Search Report and Written Opinion mailed Nov. 26, 2021 in International Application No. PCT/US2021/038627.

* cited by examiner

*Primary Examiner* — Valerie Rodriguez-Garcia
*Assistant Examiner* — Jed A Kucharczk
(74) *Attorney, Agent, or Firm* — MEDLER FERRO WOODHOUSE & MILLS PLLC

(57) ABSTRACT

The invention relates to a method of inhibiting viral replication by topically administering imiquimod, {1-(2-methylpropyl)-1H-imidazo[4,5-c]-quinolin-4-amine} or by administering imiquimod cocrystals (made with ferulic, acetic, tartaric, citric or coumaric acid). Another aspect of the invention is a method of preventing or reducing the severity of an infection by topically administering by imiquimod, or one of these cocrystals. Another aspect is administering imiquimod or one of these cocrystals in a nasal spray.

14 Claims, 16 Drawing Sheets

ANTIVIRAL THERAPY WITH IMIQUIMOD AND COCRYSTALS THEREOF

BACKGROUND OF THE INVENTION

There are hundreds of coronaviruses, most of which circulate among such animals as pigs, camels, bats and cats. Sometimes those viruses jump to humans—called a spill-over event—and can cause disease. Four of the seven known coronaviruses that sicken people cause only mild to moderate disease. Three can cause more serious, even fatal, disease. SARS coronavirus (SARS-CoV) emerged in November 2002 and caused severe acute respiratory syndrome (SARS). That virus disappeared by 2004. Middle East respiratory syndrome (MERS) is caused by the MERS coronavirus (MERS-CoV). Transmitted from an animal reservoir in camels, MERS was identified in September 2012 and continues to cause sporadic and localized outbreaks.

The third novel coronavirus to emerge in this century is called SARS-CoV-2. It causes coronavirus disease 2019 (COVID-19), which emerged from China in December 2019 and was declared a global pandemic by the World Health Organization on Mar. 11, 2020.

Fighting the new coronavirus SARS-Cov-2, and the disease it causes, COVID-19, is a top priority in medical research and pharmaceutical development. Hundreds of organizations are working on innovations to reduce the impact of the disease and prevent further infection. However, current therapy options for COVID-19 have various limitations, and none have yet been shown to be effective in early stages of infection.

Antiviral therapies being investigated include the following drugs: Remdesivir showed promise in early clinical trials in which results indicated that remdesivir speeds recovery and reduces hospital stays from 15 to 11 days, but it is currently approved for emergency use only for hospitalized patients with severe disease. Chloroquine and hydroxychloroquine have insufficient clinical data indicating efficacy, and on Jun. 15, 2020, the US Food and Drug Administration revoked Emergency Use Authorization of oral formulations of hydroxychloroquine and chloroquine for treatment of COVID-19. Lopinavir/Ritonavir provide no significant improvement over standard care. A combination of hydroxychloroquine and azithromycin is currently used, but insufficient clinical data supports use and they are potentially toxic at higher doses.

Immune-based therapies being investigated include the following: Interferons, which are effective as monotherapy or in combination with other anti-viral drugs. Coronavirus-19 is sensitive to interferon treatment. However, concern for inducing a "cytokine bomb" in severely ill patients limits use. COVID-19 convalescent plasma and SARS-CoV-2 Immune Globulins are being investigated but insufficient data is available to support use. Interleukin-1 and Interleukin-6 inhibitors (e.g., Tocilizumab) and JAK inhibitors are being investigated, but insufficient data is available. Anti-inflammatory drugs, such as glucosteroids, may be beneficial if used in early phase of infection. Finally, vaccines have promising early data, but long term impact due to viral mutation is unknown. In addition, scale up presents significant challenges. Thus, there is a dire need for an effective therapy, particularly one which might prevent infection or inhibit viral replication in the early stage of infection.

SUMMARY OF THE INVENTION

The invention relates to providing therapy or prophylaxis for certain viral or fungal infections by administering imiquimod, {1-(2-methylpropyl)-1H-imidazo[4,5-c]-quinolin-4-amine} and/or an imiquimod cocrystal made with one of the coformers ferulic acid, acetic acid, citric acid, coumaric acid, and tartaric acid. These cocrystals are named IMQ-Fe, IMQ-Ac, IMQ-Ci, IMQ-Co, and IMQ-Tar, respectively. In some aspects, the imiquimod or cocrystal is administered topically, e.g., as a nasal spray. Another aspect of the invention is administering imiquimod or one of these cocrystals in a nasal spray, which means that the composition is formulated as a sprayable composition with suitable excipients and provides drug delivery through the nasal mucosa.

In one embodiment, the invention relates to a method of increasing interferon levels in a subject in need thereof comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

In another embodiment, the invention relates to a method of inhibiting SARS-CoV-2 viral replication in a subject in need thereof comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

Another aspect of the invention relates to a method of preventing, or providing prophylaxis of, a SARS-COV-2 infection in a subject in need thereof, comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

The invention also provides a method of reducing the severity of a SARS-COV-2 infection in a subject in need thereof, comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

In another embodiment, the invention provides a method of treating a SARS-COV-2 infection in a subject in need thereof, comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

In yet another embodiment, the invention provides a method of treating Long COVID in a subject in need thereof, comprising administering to the subject a therapeutically effective amount of an active pharmaceutical ingredient selected from the group consisting of imiquimod, IMQ-Fe, IMQ-Ac, IMQ-Ci, IMQ-Co, and/or IMQ-Tar.

Another embodiment of the invention is a method of treating postural orthostatic tachycardia syndrome (POTS) in a subject in need thereof, comprising administering to the subject a therapeutically effective amount of an active pharmaceutical ingredient selected from the group consisting of imiquimod, IMQ-Fe, IMQ-Ac, IMQ-Ci, IMQ-Co, and/or IMQ-Tar.

In another embodiment of any of the methods of the invention, the subject has been infected with SARS-COV-2.

In yet another embodiment of any of the methods of the invention, the subject has been exposed to SARS-COV-2.

In another aspect, the invention provides a method of inhibiting viral replication in a subject in need thereof comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar.

In one embodiment of this method, the subject is infected with a virus selected from the group consisting of influenza A virus, respiratory syncytial virus (RSV), varicella-zoster virus, herpes simplex virus (HSV), human immunodeficiency virus (HIV/AIDS), human papillomavirus (HPV), Middle East respiratory syndrome (MERS) coronavirus (MERS-CoV), Zika virus, Dengue virus, and mumps measles and rubella (MMR) virus.

The invention also relates to a method of treating a viral infection in a subject in need thereof comprising administering to the subject a therapeutically effective amount of an active pharmaceutical ingredient selected from the group consisting of: imiquimod, IMQ-Fe, IMQ-Ac, IMQ-Ci, IMQ-Co, and IMQ-Tar, wherein the subject has an infection selected from the group consisting of chicken pox, shingles, herpes, influenza, HIV/AIDS, viral mononucleosis, viral pneumonia, HPV, MMR, viral gastroenteritis, viral hepatitis, viral meningitis, Zika virus, Dengue virus, and mucormycosis.

In one embodiment, the subject is infected with mucormycosis and has been diagnosed with COVID-19 within the previous 8 weeks.

In yet another embodiment of any of the methods of the invention, the active pharmaceutical ingredient is administered topically, e.g., to the nasopharyngeal area. In another aspect, the active pharmaceutical ingredient is delivered in a nasal spray. In yet another aspect, the active pharmaceutical ingredient is in a composition formulated for topical administration.

In another aspect of any of the methods of the invention, the active pharmaceutical ingredient is administered to the nasopharyngeal area of the subject by spraying a composition comprising the active pharmaceutical ingredient into the nasal passage.

In another aspect of any of the methods of the invention, the dose of the active pharmaceutical ingredient administered is about 10 to about 100 μl of spray containing about 5 to about 50 μg of the active pharmaceutical ingredient.

In another aspect of any of the methods of the invention, the dose administered is about 10 to about 100 μl of spray containing about 10 to about 40 μg of the active pharmaceutical ingredient.

In yet another aspect of any of the methods of the invention, the dose administered is 50 μl of spray containing about 25 μg of the active pharmaceutical ingredient.

In some embodiments of the method, the active pharmaceutical ingredient is administered once per day, in other embodiments it may be administered more frequently, e.g., twice per day, three times per day, or four times per day.

In some embodiments, the method further comprises administering ferulic acid to the subject.

The invention also relates to a sprayable liquid composition, the composition comprising an active pharmaceutical ingredient selected from the group consisting of: imiquimod, IMQ-Fe, IMQ-Ac, IMQ-Ci, IMQ-Co, and IMQ-Tar, and one or more pharmaceutically acceptable excipients. In one embodiment, the composition is a nasal spray formulation. In another embodiment, the composition is in a spray bottle. The composition may be administered, e.g., to the nasopharyngeal area of a subject, through the nasal passage. In some embodiments of the invention, the concentration of the active pharmaceutical ingredient is about 5 μg/100 μL to about 80 μg/100 μL. In other embodiments, the concentration of the active pharmaceutical ingredient is about 10 μg/100 μL to about 40 μg/100 μL. In yet other embodiments, the concentration of the active pharmaceutical ingredient is about 10 μg/100 μL, about 20 μg/100 μL, about 25 μg/100 μL, about 30 μg/100 μL, about 40 μg/100 μL, about 45 μg/100 μL, about 50 μg/100 μL, about 60 μg/100 μL, or about 70 μg/100 μL. In some embodiments of the methods described above, the method comprises administering the sprayable liquid composition to the nasopharyngeal area of the subject.

The invention also provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in increasing interferon levels in a subject in need thereof.

The invention also provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in inhibiting SARS-Cov-2 viral replication in a subject in need thereof. In some embodiments, the subject has been exposed to or has been infected with SARS-CoV-2.

In another aspect, the invention provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in preventing a SARS-Cov-2 infection in a subject. In some embodiments, the subject has been exposed to SARS-CoV-2.

Yet another aspect of the invention is a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in reducing the severity of a SARS-CoV-2 infection in a subject in need thereof.

In another embodiment, the invention provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in treating a SARS-COV-2 infection in a subject in need thereof.

The invention also provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in inhibiting viral replication in a subject in need thereof. In some aspects, the subject is infected with a virus selected from the group consisting of influenza A virus, RSV, varicella-zoster virus, HSV, HIV/AIDS, HPV, MERS-CoV, Zika virus, Dengue virus, and MMR virus.

The invention also provides a pharmaceutical composition comprising an effective amount of an active pharmaceutical ingredient selected from the group consisting of: imiquimod, IMQ-Fe, IMQ-Ac, IMQ-Ci, IMQ-Co, and IMQ-Tar, for use in treating a viral infection in a subject in need thereof, wherein the subject has an infection selected from the group consisting of chicken pox, shingles, herpes, influenza, HIV/AIDS, viral mononucleosis, viral pneumonia, HPV, MMR, viral gastroenteritis, viral hepatitis, viral meningitis, Zika virus, Dengue virus, and mucormycosis.

In one embodiment, the subject is infected with mucormycosis and has been diagnosed with COVID-19 within the previous 8 weeks In some embodiments, the pharmaceutical composition is formulated for topical administration. In other aspects, the pharmaceutical composition is a sprayable liquid composition. In some embodiments, the pharmaceutical composition is formulated as a nasal spray.

In some embodiments of the invention, the concentration of the active pharmaceutical ingredient in the pharmaceutical composition is about 5 μg/100 μL to about 80 μg/100 μL. In other embodiments, the concentration of the active pharmaceutical ingredient is about 10 μg/100 μL to about 40 μg/100 μL. In yet other embodiments, the concentration of the active pharmaceutical ingredient is about 10 μg/100 μL, about 20 μg/100 μL, about 25 μg/100 μL, about 30 μg/100 μL, about 40 μg/100 μL, about 45 μg/100 μL, about 50 μg/100 μL, about 60 μg/100 μL, or about 70 μg/100 μL.

In some aspects, the pharmaceutical composition further comprises ferulic acid.

In another aspect, the invention provides a sprayable composition, comprising an active pharmaceutical ingredient selected from the group consisting of: imiquimod, IMQ-Fe, IMQ-Ac, IMQ-Ci, IMQ-Co, and IMQ-Tar and one or more pharmaceutically acceptable excipients. In another embodiment, the sprayable composition is for use in application to the nasal mucosa.

The following novel cocrystals of imiquimod may be used in the methods or compositions of the invention: IMQ-Fe, a ferulic acid cocrystal of imiquimod; IMQ-Ac, an acetic acid cocrystal of imiquimod; IMQ-Co, a coumaric acid cocrystal of imiquimod; IMQ-Ci, a citric acid cocrystal of imiquimod; and IMQ-Tar, a tartaric acid cocrystal of imiquimod.

In one embodiment of the invention, the powder X-ray diffraction pattern of IMQ-Fe is shown in FIG. 1. In another embodiment of the invention, the DSC thermogram of IMQ-Fe is shown in FIG. 3. In yet another embodiment of the invention, the TGA curve of IMQ-Fe is shown in FIG. 4. In one embodiment of the invention the IR spectrum of IMQ-Fe, over the wavelength range of 3400-600 $cm^{-1}$, is shown in FIG. 9.

In another embodiment of the invention, the molar ratio of imiquimod to ferulic acid in the cocrystal IMQ-Fe is from 0.8:1.0 to 1.0:0.8. In another aspect of the invention, the ratio of imiquimod to ferulic acid in the cocrystal IMQ-Fe is equimolar.

In another embodiment, the cocrystal IMQ-Fe has a PXRD pattern using Cu-Kα radiation, expressed as 2Θ angles, with at least two peaks at positions selected from the following group: 12.3±0.2°, 13.3±0.2°, 15.1±0.2°, 17.2±0.2°, 17.7±0.2°, 17.9±0.2°, 18.7±0.2°, 19.5±0.2°, 19.9±0.2°, 23.5±0.2°, 24.7±0.2°, 25.7±0.2°, 26.9±0.2°, 27.5±0.2°, 28.1±0.2°, 28.9±0.2°, 29.5±0.2°, 30.4±0.2°, and 31.5±0.2°. In another aspect of the invention, the PXRD pattern has at least 4 peaks selected from this group. In yet another aspect, the cocrystal IMQ-Fe has a PXRD pattern, using Cu-Kα radiation, expressed as 2Θ angles, with peaks at positions 13.3±0.2° and 28.1±0.2°.

In one embodiment, the cocrystal IMQ-Fe, has a single melting point at 225-227° C. as measured by DSC. In another embodiment, the cocrystal IMQ-Fe, has a single melting point at 226.4±0.2° C. as measured by DSC. In yet another embodiment, the cocrystal IMQ-Fe has a single melting point at 226.4° C., as measured by DSC.

In one aspect, the cocrystal IMQ-Fe is stable up to 180° C. with negligible weight loss as measured by TGA.

In another aspect of the invention, the cocrystal IMQ-Fe is anhydrous.

In yet another aspect, the Fourier-transform infrared spectrum of the cocrystal IMQ-Fe has a carboxylic acid peak at 1700.90±0.5 $cm^{-1}$.

In one embodiment, the cocrystal IMQ-Fe was prepared by grinding equimolar amounts of imiquimod and ferulic acid in methanol.

In one embodiment of the invention, the powder X-ray diffraction pattern of IMQ-Ac is shown in FIG. 12. In another embodiment of the invention, the DSC thermogram of IMQ-Ac is shown in FIG. 13. In one embodiment of the invention, the TGA curve of IMQ-Ac is shown in FIG. 14.

In one aspect of the invention, the molar ratio of imiquimod to acetic acid in the cocrystal IMQ-Ac is from 0.8:1.0 to 1.0:0.8 In another aspect of the invention, the ratio of imiquimod to acetic acid in the cocrystal IMQ-Ac is equimolar.

In yet another aspect, the cocrystal IMQ-Ac has a PXRD pattern using Cu-Kα radiation, expressed as 2Θ angles, with at least two peaks at positions selected from the following group: 5.9±0.2°, 6.7±0.2°, 7.9±0.2°, 9.0±0.2°, 9.8±0.2°, 12.9±0.2°, 17.1±0.2°, 20.8±0.2°, 22.7±0.2°, 25.5±0.2°, 26.1±0.2°, and 27.1±0.2°. In another aspect, the PXRD pattern has at least 4 peaks selected from this group. In another embodiment, the cocrystal IMQ-Ac has a PXRD pattern using Cu-Kα radiation, expressed as 2Θ angles, with peaks at positions 6.7±0.2° and 9.0±0.2°.

In yet another embodiment, the cocrystal IMQ-Ac has an endotherm at 72.5±0.2° C. and at 96.1±0.2° C. as measured by DSC.

In another embodiment, the cocrystal IMQ-Ac was prepared by grinding equimolar amounts of imiquimod and acetic acid in methanol.

In one embodiment of the invention, the powder X-ray diffraction pattern of IMQ-Co is shown in FIG. 15. In another embodiment of the invention, the DSC thermogram of IMQ-Co is shown in FIG. 16. In yet another embodiment of the invention, the TGA curve of IMQ-Co is shown in FIG. 17.

In one aspect of the invention, the molar ratio of imiquimod to coumaric acid in the cocrystal IMQ-Co is from 0.8:1.0 to 1.0:0.8. In yet another aspect, the ratio of imiquimod to coumaric acid in the cocrystal IMQ-Co is equimolar.

In an embodiment of the invention, the cocrystal IMQ-Co has a PXRD pattern, using Cu-Kα radiation, with at least two peaks at positions selected from the following group: 9.0±0.2°2Θ, 10.2±0.2°2Θ, 15.6±0.2°2Θ, 16.2±0.2°2Θ, 18.2±0.2°2Θ, 23.2±0.2°2Θ, 25.5±0.2°2Θ, and 27.5±0.2°2Θ. In another embodiment, the PXRD pattern has at least 4 peaks selected from this group. In yet another embodiment, the cocrystal IMQ-Co has a PXRD pattern using Cu-Kα radiation, expressed as 2Θ angles, with peaks at positions 9.0±0.2° and 25.5±0.2°.

In one aspect of the invention, the cocrystal IMQ-Co has an endotherm at 219.2±0.2° C. and/or at 134.1±0.2° C. as measured by DSC. In one aspect of the invention, the cocrystal IMQ-Co has an endotherm at 219.2±0.2° C. as measured by DSC.

In another aspect of the invention, the cocrystal IMQ-Co has a 4.6±0.5% weight loss at 150±2.0° C. as measured by TGA.

In yet another aspect, the cocrystal IMQ-Co was prepared by grinding equimolar amounts of imiquimod and coumaric acid in methanol.

In one aspect of the invention, the powder X-ray diffraction pattern of IMQ-Ci is shown in FIG. 18. In another aspect of the invention, the DSC thermogram of IMQ-Ci is shown in FIG. 19. In yet another aspect of the invention, the TGA curve of IMQ-Ci is shown in FIG. 20.

In one embodiment of the invention, the molar ratio of imiquimod to citric acid in the cocrystal IMQ-Ci is from 2.2:1 to 2.0:0.8. In another embodiment, the imiquimod and citric acid in the cocrystal IMQ-Ci have a molar ratio of 2:1.

In yet another embodiment, the cocrystal IMQ-Ci has a PXRD pattern, using Cu-Kα radiation, expressed as 2Θ angles, with at least two peaks at positions selected from the following group: 5.2±0.2°, 5.8±0.2°, 7.3±0.2°, 13.1±0.2°, 13.7±0.2°, 15.2±0.2°, 21.9±0.2°, 22.7±0.2°, 23.4±0.2°, and 25.3±0.2°. In yet another embodiment, the PXRD pattern has at least 4 peaks selected from this group. In another aspect, the cocrystal IMQ-Ci has a PXRD pattern using Cu-Kα radiation, expressed as 2Θ angles, with peaks at positions 5.8±0.2° and 23.4±0.2°.

In one aspect, the cocrystal IMQ-Ci has an endotherm at 121.1±0.2° C. and/or at 205.5±0.2° C. as measured by DSC. In one aspect, the cocrystal IMQ-Ci has an endotherm at 205.5±0.2° C. as measured by DSC.

In another aspect, the cocrystal IMQ-Ci has a 5.0±0.5% weight loss at 120±2.0° C. as measured by TGA.

In yet another aspect, the cocrystal IMQ-Ci was prepared by grinding imiquimod and citric acid in an organic solvent, wherein the imiquimod and citric acid have a molar ratio of 2:1.

In one embodiment of the invention, the powder X-ray diffraction pattern of IMQ-Tar is shown in FIG. 21. In another embodiment of the invention, the TGA curve of IMQ-Tar is shown in FIG. 22.

In one aspect of the invention, the molar ratio of imiquimod to tartaric acid in the cocrystal IMQ-Tar is from 2.2:1 to 2.0:0.8. In yet another aspect of the invention, the imiquimod and tartaric acid in the cocrystal IMQ-Tar have a molar ratio of 2:1.

In yet another aspect, the cocrystal IMQ-Tar has a PXRD pattern using Cu-Kα radiation, expressed as 2Θ angles, with at least two peaks at positions selected from the following group: 6.6±0.2°, 8.5±0.2°, 13.3±0.2°, 14.7±0.2°, 17.8±0.2°, 19.0±0.2°, 20.9±0.2°, 22.4±0.2°, 26.1±0.2°, 27.5±0.2°, and 29.8±0.2°. In another aspect, the PXRD pattern has at least 4 peaks selected from this group. In yet another aspect, the cocrystal IMQ-Tar has a PXRD pattern using Cu-Kα radiation, expressed as 2Θ angles, with peaks at positions 8.5±0.2° and 26.1±0.2°.

In another embodiment of the invention, the cocrystal IMQ-Tar does not melt below 200° C. as measured by DSC.

In another embodiment of the invention, the cocrystal IMQ-Tar has a 5.2±0.5% weight loss at 170±2.0° C. as measured by TGA.

In yet another embodiment, the cocrystal IMQ-Tar was prepared by grinding imiquimod and tartaric acid in methanol, wherein the imiquimod and tartaric acid have a molar ratio of 2:1.

The cocrystals of the invention have advantageous properties, compared to known forms of imiquimod, such as higher solubility in certain solvents, and improved hygroscopicity, morphology, processability and phase stability. Thus, the cocrystal forms of the present invention are more suitable than imiquimod for use as the active ingredient in pharmaceutical formulations. For example, the known form of imiquimod has low water solubility and very low topical bioavailability.

DETAILED DESCRIPTION OF THE INVENTION

Figure 1:
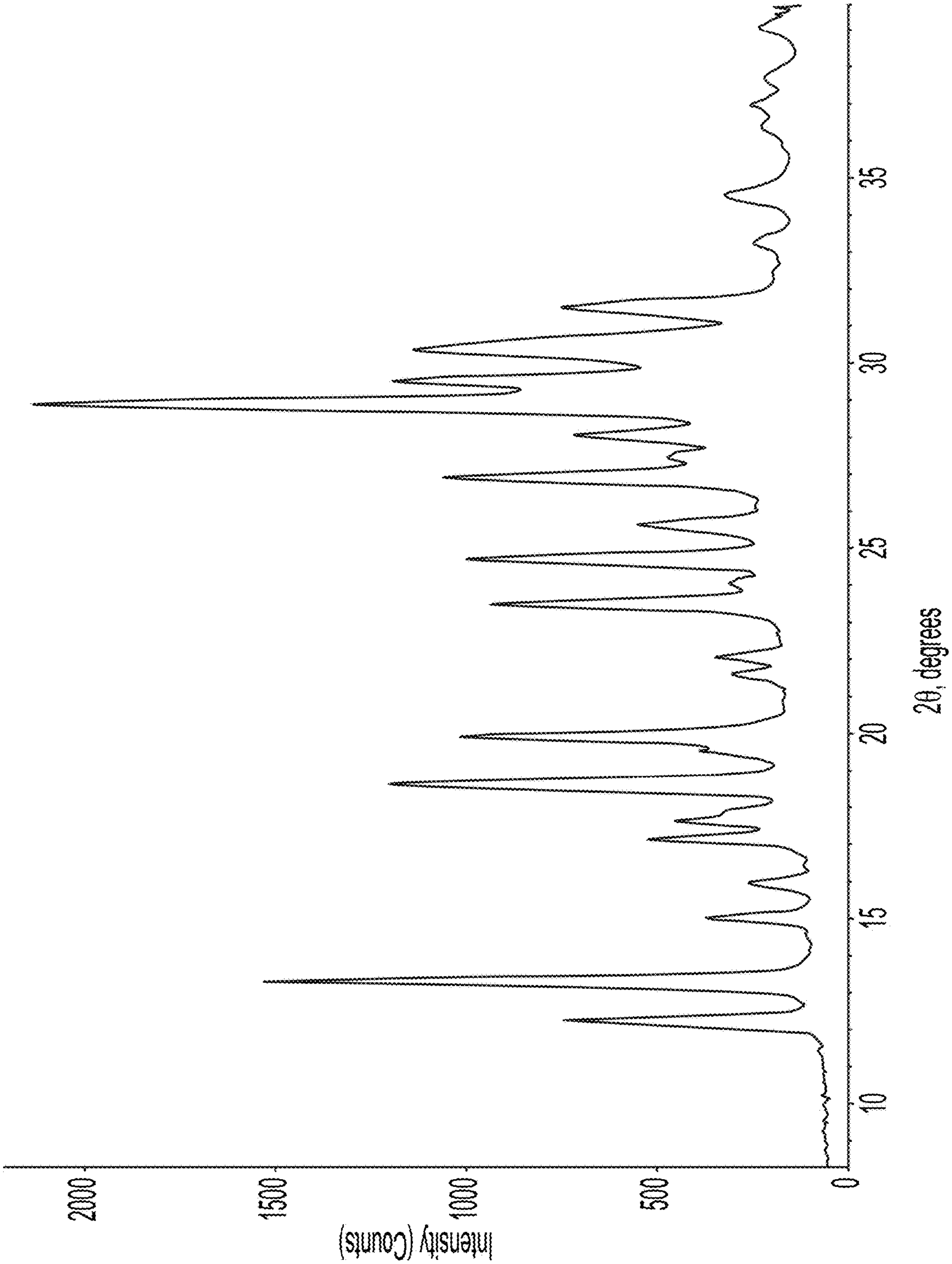
FIG. 1 is the PXRD pattern of the imiquimod-ferulic acid cocrystal IMQ-Fe.

Imiquimod is a synthetic small molecule active pharmaceutical ingredient (API). It is a toll-like receptor (TLR) agonist which induces anti-tumor activity by activating the immune system through this receptor (TLR 7), which stimulates both innate and adaptive immunity. Imiquimod is currently available as a cream with indications for actinic keratosis, superficial basal cell carcinoma and external genital warts. Imiquimod in a cream formulation suffers from poor bioavailability (0.6%) leading to poor efficacy. Around 97-98% of actinic keratosis patients and 90%-100% basal cell carcinoma patients using imiquimod cream experience painful erythema of the skin due to a high amount of residual drug remaining on the skin for a minimum of 8 hours/day for several weeks due to minimal absorption of imiquimod from the cream.

Hallmarks of the SARS-CoV-2 infection, Coronavirus-2019 (COVID-19)-infections are a delayed or suppressed Type I IFN response, fast viral peak replication, a suppressed innate immune response, and a hyperinflammatory condition.

Imiquimod recognizes pathogen associated molecular patterns (PAMPs). It initiates innate immunity and induces adaptive immune reactions, and viral clearance.

Ferulic acid (abbreviated "Fe" herein) has inhibitory activity of virus growth and replication and may provide a protective function against viruses.

The inventors have discovered that imiquimod, an immunotherapy agent with a well-established safety profile, can be used to inhibit viral replication, and to prevent (provide prophylaxis) and treat viral diseases such as COVID-19, chicken pox, shingles, herpes, influenza, HIV/AIDS, viral mononucleosis, viral pneumonia, HPV, MMR, viral gastroenteritis, viral hepatitis, viral meningitis, Zika virus, Dengue virus, and mucormycosis.

The inventors have also discovered a way to modify imiquimod to improve its absorption. In animal studies, discussed in Example 1, below, the inventors have shown that imiquimod and the ferulic acid cocrystal of imiquimod (IMQ-Fe) significant increases systemic interferon levels quickly when applied topically. In addition, the inventors discovered that significantly higher levels of interferon are achieved with IMQ-Fe than imiquimod because IMQ-Fe is more soluble and more bioavailable than imiquimod.

Imiquimod is a potent TLR-7/8 Agonist. Imiquimod induces (IMQ) TLR-7 and TLR-8 mediated signaling cascades. It is a potent inducer of interferons (IFNs), inducing levels of circulating IFN activity as high as 2,000 U/ml detected in treated mice. Interferon I directly inhibits virus replication and indirectly modulates host immune response. Imiquimod induces Type II interferon γ, important in clearing virus infected cells. Imiquimod activates dendritic cells, monocytes, macrophages.

Ferulic acid has antiviral activity. It can prevent and control RNA virus infections by amplifying the signaling functions of TLR7 in evoking type 1 interferon production. Ferulic acid also has protective activity. It is a mucous membrane protectant and has protective effects against induced lung inflammation. In addition, it up-regulates interferon-γ and IL-10, ameliorates airway inflammatory response and exerts potential protective effects against respiratory injury (in mice).

The inventors have discovered that imiquimod in combination with Ferulic acid has a synergistic anti-viral activity.

In addition, the inventors have discovered a nasal spray formulation, containing imiquimod or one of the imiquimod cocrystals discussed below, that can be administered quickly and easily to directly address the early site of viral infection. This product increases interferon levels markedly and interferons have been shown to inhibit viral growth. Imiquimod, and the cocrystals of the invention, can also induce other immune markers to fight the infection.

At risk individuals, e.g., care home residents, health care workers, etc., could use the nasal spray to prevent infection or reduce the rapid progression of a viral disease. The product could be used prophylactically and can be mass produced at an attractive cost.

Benefits of the methods and compositions of the invention include the following: They can provide a reduction in viral replication, and thus may be used as a vaccine adjuvant. The methods and compositions of the invention induce a powerful immune response. Imiquimod produces Type I and II IFNs and preserves adaptive immunity for effective viral clearance. Imiquimod is also a lung protectant. It significantly reduces airway and lung inflammation, preserves the oxidative burst capacity of inflammatory cells, and does not increase TNF, IL1α and IL6, which are elevated in COVID-19 ICU patients.

In addition, imiquimod (IMQ) and ferulic acid (Fe) can provide synergistic antiviral effects. IMQ-Fe increases the immune response over imiquimod alone.

Moreover, the compositions of the invention are easy to use. They are self-administered, provide quick absorption, and can be used for preventative/prophylactic use. They may be particularly valuable in target populations, such as vulnerable populations and front-line health workers.

In summary, the methods and compositions of the invention address many of the short-comings of investigative therapies for COVID-19 and other viral infections. The invention provides a significant increase in interferon levels in animal studies from a quickly absorbing drug/formulation combination. The invention provides a preventative medication that can be used prophylactically. Imiquimod is safe, and the inventors have found a way to reduce the drug concentration/dose, and thus possibly increase safety or reduce adverse effects. Moreover, the compositions of the invention can be scaled up efficiently.

The inventors have also discovered novel crystalline forms of imiquimod, described herein, that the inventors believe to be cocrystals. Thus, the invention also relates to the following novel cocrystals of imiquimod: IMQ-Fe, a ferulic acid cocrystal of imiquimod; IMQ-Ac, an acetic acid cocrystal of imiquimod; IMQ-Co, a coumaric acid cocrystal of imiquimod; —IMQ-Ci, a citric acid cocrystal of imiquimod; and IMQ-Tar, a tartaric acid cocrystal of imiquimod.

A drug cocrystal is the crystalline form made from an active pharmaceutical ingredient (API) in combination with one or more coformer(s) in a fixed stoichiometric ratio. A cocrystal can be a multi-component crystal, such as a binary cocrystal formed between two neutral solids or a pluralistic cocrystal. Unlike salts, where the components of the crystal lattice are in an ionized state, the cocrystals' components are in a neutral state and interact through non-ionic interactions. Hence, one difference between salts and cocrystals is that in salt formation there is a proton transfer and ionization, while this does not occur in a cocrystal. Rather, the interactions between API and coformer in a cocrystal are not ionic bond interactions nor covalent bond interactions. They are weak interactions such as hydrogen bonds, van der Waals forces, π-π interactions or halogen bonds.

Cocrystals can exist as polymorphs, or as hydrates or solvates.

Therapeutic efficacy is a primary concern for an API, but this efficacy can be affected by the pharmacological properties of the API. The salt and/or solid-state form (e.g., crystalline or amorphous forms) of a drug candidate impact its pharmacological properties. For example, each salt or each solid form of a drug candidate can have different solid state (physical and chemical) properties. The differences in physical properties exhibited by different solid forms of an API, such as a molecular complex, cocrystal, salt, or polymorph of the original compound, can affect pharmaceutical parameters of the API. For example, storage stability, compressibility and density can be important in formulation and product manufacturing. In addition, solubility and dissolution rate, which may be important factors in determining bioavailability, may be affected. Therefore, the particular solid state form of the API can significantly impact a number of factors, including the selection of a compound as an API, the pharmaceutical dosage form, the optimization of manufacturing processes, absorption by the body, and efficacy.

Active drug molecules may be made into pharmaceutically acceptable salts for therapeutic administration to the patient. Crystalline salts of a drug may offer advantages over the free form of the compound, such as improved solubility, stability, processing improvements, and different crystalline salt forms may offer greater or lesser advantages over one another. However, crystalline salt forms are not predictable, and, in fact, are not always possible to achieve. Moreover, there is no way to predict the properties of a particular crystalline salt of a compound until it is formed. As such, finding the right conditions to obtain a particular crystalline salt form of a compound, with pharmaceutically acceptable properties is challenging.

By cocrystallizing an API or a salt of an API with a coformer (the other component of the cocrystal), one creates a cocrystal—a new solid state form of the API which has unique properties relative to existing solid forms of the API or its salt. For example, a cocrystal may have different dissolution and/or solubility properties than the active agent itself or its salt. Improved solubility may lead to increased concentration in solution, which may, in turn, lead to increased bioavailability of the compound. Cocrystals containing APIs can, therefore, be used to deliver APIs therapeutically. New drug formulations comprising cocrystals of APIs with pharmaceutically acceptable coformers may, in some cases, have superior properties over existing drug formulations. However, cocrystal formation is also not unpredictable, and not always possible. Moreover, there is no way to predict the properties of a particular cocrystal of a compound until it is formed. As such, finding the right conditions to obtain a particular cocrystal of a compound, with pharmaceutically acceptable properties, is challenging.

The cocrystals of the invention have advantageous properties, compared to known forms of imiquimod, such as higher solubility in certain solvents, acceptable hygroscopicity, morphology, processability and phase stability. The cocrystal forms of the present invention are more suitable for use as the active ingredient in pharmaceutical formulations. For example, the known form of imiquimod has low water solubility and very low topical bioavailability.

A crystalline form of a compound, a crystalline salt of the compound, or a cocrystal containing the compound or its salt form generally possesses distinct crystallographic, thermal and spectroscopic properties when compared to other crystalline forms having the same chemical composition.

Crystallographic and spectroscopic properties of a particular form may be measured by PXRD, or single crystal X-ray crystallography, among other techniques.

Fourier-transform IR spectroscopy (FTIR), which can be used for the simultaneous study of the spectra of the cocrystals' individual components and of their final mixture with polymer matrices, etc., is an important tool in detecting cocrystal formation and in the elucidation of their structures. The cocrystal provides a different spectrum from that of the components' mixture due to the presence of hydrogen bonds, especially when carboxylic acid is used as a coformer and when a neutral hydrogen bond O—H _ _ _ N is formed between an acid and a base. Clear IR spectra differences are observed between a neutral carboxylic acid functional group and a carboxylic anion. Neutral carboxylate (—COOH) shows a strong tension band of C═O at about 1700 cm).

A particular crystalline form of a compound, its salt, or a cocrystal of the compound, also often exhibit distinct thermal behavior. Thermal behavior can be measured in the laboratory by techniques such as capillary melting point, TGA, or DSC. The thermal behavior of an API, such as its melting point, can impact formulation of the API. The melting point of the solid form of a drug is optionally high enough to avoid melting or plastic deformation during standard processing operations, as well as concretion of the drug by plastic deformation on storage. For some formulation processing methods, higher melting points may be desirable, e.g., above about 100° C.

Effective cocrystal preparation methods in use today can be classified as: (1) solid (neat grinding, solvent-assisted grinding, sonication); or (2) solvent-based (slurring, solvent evaporation, crystallization from solution or active cocrystallization and antisolvent addition). [Karagianni, A. et al., "Pharmaceutical Cocrystals: New Solid Phase Modification Approaches for the Formulation of APIs," *Pharmaceutics,* 10, 18, 2018; Qiao, N et al., "Pharmaceutical cocrystals: An overview", International Journal of Pharmaceutics, 419, 2011. 1-11.].

The cocrystals of the invention may be made by solid state grinding of imiquimod with ferulic acid, acetic acid, coumaric acid, citric acid, or tartaric acid in the presence of methanol or another suitable solvent, as described below. The solvent may be, e.g., methanol, acetone, ethanol, acetonitrile, or another organic solvent. The amount of solvent added is about 100 μL-1.0 mL per 1.0 g of total material (imiquimod±coformer). For lab scale batches imiquimod, coformer and solvent are mixed for about 15 to about 45 minutes. For 1 gram of material, mixing will be done for about 30-45 minutes. For larger scale production, the mixing period may need to be increased. If the material is ground for about 30 minutes, a small amount of methanol should be added at regular intervals, such as about every 10 minutes. Batches are made at room temperature, 15-22° C., preferably 18-22° C. The solids (imiquimod and coformer) will partially dissolve during grinding, such that they form a wet powder or paste. During grinding most of the solvent will evaporate. The mixture can be dried in a vacuum oven at room temperature.

In one embodiment, the cocrystals of the present invention can formulated as pharmaceutical dosage forms. Thus, the invention also relates to pharmaceutical compositions containing the novel cocrystals and one or more pharmaceutically acceptable excipients. Depending on the type of pharmaceutical composition, the pharmaceutically acceptable excipient may be chosen from any one or a combination of excipients known in the art. The choice of the pharmaceutically acceptable excipient depends upon the pharmaceutical form and the desired method of administration to be used. Remington: The Science and Practice of Pharmacy. 22 ed. London, UK: Pharmaceutical Press; 2012, discloses various excipients used in formulating pharmaceutical compositions and techniques for the preparing pharmaceutical compositions.

Definitions

As used herein, the following words and phrases are generally intended to have the meanings as set forth below, except to the extent that the context in which they are used indicates otherwise.

The terms "imiquimod" and "IMQ" refer to the compound with the chemical designation 1-(2-methylpropyl)-1H-imidazo[4,5-c]quinolin-4-amine. Imiquimod has a molecular formula of $C_{14}H_{16}N_4$ and a molecular weight of 240.3. It has the following structure:

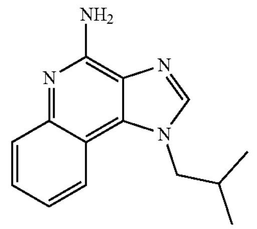 [SMILES: CC(C)Cn1cnc2c(N)nc3ccccc3c21]

Ferulic acid (abbreviated "Fe" herein) has the following structure:

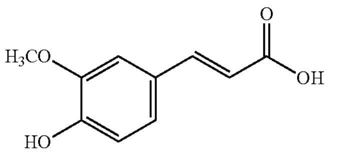 [SMILES: COc1cc(/C=C/C(=O)O)ccc1O]

As used herein, the terms IMQ-Fe, ferulic acid cocrystal of imiquimod, imiquimod-ferulic acid cocrystal, and variations thereof, are used interchangeably to refer to the novel cocrystal formed from imiquimod and ferulic acid described herein. An alternative name for IMQ-Fe is IMQ-FA.

As used herein, the terms IMQ-Ac, acetic acid cocrystal of imiquimod, imiquimod-acetic acid cocrystal, and variations thereof, are used interchangeably to refer to the novel cocrystal formed from imiquimod and acetic acid described herein.

As used herein, the terms IMQ-Co, coumaric acid cocrystal of imiquimod, imiquimod-coumaric acid cocrystal, and variations thereof, are used interchangeably to refer to the novel cocrystal formed from imiquimod and coumaric acid described herein.

As used herein, the terms IMQ-Ci, citric acid cocrystal of imiquimod, imiquimod-citric acid cocrystal, and variations thereof, are used interchangeably to refer to the novel cocrystal formed from imiquimod and citric acid described herein.

As used herein, the terms IMQ-Tar, tartaric acid cocrystal of imiquimod, imiquimod-tartaric acid cocrystal, and variations thereof, are used interchangeably to refer to the novel cocrystal formed from imiquimod and tartaric acid described herein.

As used herein, "mole ratio" or "molar ratio" is the ratio of moles of one substance to the moles of another substance in a balanced equation.

As used herein, the term "PXRD" refers to powder x-ray diffraction. The PXRD data disclosed herein were obtained using a D8 ADVANCE; Bruker AXS, Madison, WI, USA powder diffractometer. The powder samples were exposed to Cu-Kα radiation (40 kV and 40 mA) over an angular range of 5-40° 2θ with a step size of 0.0196° and a dwell time of 0.5 s. Data analysis was performed using commercially available software (JADE Materials Data, Inc., Livermore, CA).

As used herein, the term "DSC" refers to differential scanning calorimetry. DSC data disclosed herein were obtained using a model Q2000, TA Instruments, differential scanning calorimeter equipped with a refrigerated cooling accessory. Between 5 and 10 mg of sample was hermetically sealed in an aluminum pan. All measurements were performed at a heating rate of 10° C./min under nitrogen purge (50 mL/min). The instrument was calibrated with indium.

As used herein, the term "TGA" refers to thermogravimetric analysis. TGA data disclosed herein were obtained using a TA Instruments, New Castle, DE, model Q50 TGA, thermogravimetric analyzer. 5-10 mg of sample was placed in an aluminum sample pan and heated from RT to up the melting point of the cocrystal at 10° C./min under dry nitrogen purge (50 mL/min). The TGA data were analyzed using commercial software (Universal Analysis 2000, TA Instruments, New Castle, DE).

As used herein, the term "IR" refers to infrared, and "FTIR" refers to Fourier-transform IR spectroscopy. The FTIR spectroscopy data disclosed herein was obtained using a Vertex 70, Bruker, Ettlingen, Germany, spectrometer, equipped with a globar mid-IR source), using an attenuated total reflectance (ATR) accessory (single reflection germanium crystal) and a DLaTGS detector. The resolution was 4 $cm^{-1}$, and 64 scans were acquired in the range of 4000-400 $cm^{-1}$. The peak positions were determined using OPUS software peak picking function.

As used herein with respect to the various analytical techniques described herein and data generated therefrom, the term "substantially the same as" is meant to convey that a particular set of analytical data is, within acceptable scientific limits, sufficiently similar to that disclosed herein such that one of skill in the art would appreciate that the form of the compound is the same as that of the present invention.

One of skill in the art would appreciate that certain analytical techniques, such as, for example, PXRD, TGA, DSC, IR spectroscopy, will not produce exactly the same results every time due to, for example, instrumental variation, sample preparation, operator variability, etc. By way of example only, PXRD results (i.e., peak locations, intensities, and/or presence) may vary slightly from sample to sample, despite the fact that the samples are, within accepted scientific principles, the same form, and this may be due to, for example, preferred orientation, varying degree of crystallinity, or varying solvent or water content. It is well within the ability of those skilled in the art, looking at the data as a whole, to appreciate whether such differences indicate a different form, and thus determine whether analytical data being compared to those disclosed herein are substantially the same as or similar.

In this regard, and as is commonly practiced within the scientific community, it is not intended that the exemplary analytical data of the novel cocrystal forms of imiquimod disclosed herein be met literally in order to determine whether comparative data represent the same form as that disclosed and claimed herein, such as, for example, whether each and every peak of the exemplary PXRD pattern disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form of the novel imiquimod cocrystals disclosed herein.

Further, it should be noted that varying degrees of crystallinity of a cocrystal of a compound, such as the novel cocrystals disclosed herein, may be achieved. The degree of crystallinity achieved may, for example, depend on the conditions under which a sample is prepared. Accordingly, one of skill in the art will appreciate that a particular set of analytical data may reflect a greater or lesser degree of crystallinity than the exemplary analytical data shown in the Figures herein, but appreciate that the form of the compound is the same as that disclosed and claimed herein.

The "crystalline form" in the present invention is confirmed by the powder X-ray diffraction pattern, having a unique ordered molecular arrangement or configuration within the crystal lattice. It is known to those of skill in the art that experimental errors of X-ray diffraction depend on instrument conditions, sample preparation and sample purity. The 2Θ angle of the peaks of a powder X-ray diffraction pattern usually varies slightly due to the difference in the instrument and sample. The differences in peak position may vary by 1°, 0.8°, 0.5°, 0.3°, 0.2° or 0.1° 2Θ, depending on different instruments and samples, and usually ±0.2° in differences are allowed. The relative intensities of peaks may change with the change of samples, sample preparation and other experimental conditions; therefore, the order of peak intensities should not be regarded as the only or the determining factor. Due to the effect of experimental factors including sample height, peak position may shift; generally, a small amount of peak shifting is acceptable experimental error. Hence, it is easily understood for those skilled in the field that any crystalline forms having the same or similar powder X-ray diffraction pattern as that of the crystalline form of corresponding forms in the present invention should be within the scope of the present invention.

"Pure crystalline form" as used herein refers to a pure crystalline form confirmed by powder X-ray diffraction.

The crystalline form of the cocrystals of imiquimod of the present invention is substantially pure and substantially free of any other crystalline or amorphous forms. By "substantially pure" crystalline form, it is meant that the new crystalline form comprises at least 80% by weight of the particular cocrystal, more preferably at least 90% by weight, especially at least 95% by weight, in particular at least 99% by weight.

The term "substantially all" as used herein with regard to other aspects of the present invention refers to most of the total amount, e.g., at least 80%, at least 85%, at least 90%, at least 95% or at least 99% of a total amount.

It should be noted that the novel solid forms of imiquimod disclosed herein are in crystalline form, as shown in the Figures. Without wishing to be bound, however, Applicants refer herein to the novel crystalline solid forms as "cocrystals," but note that the type of interaction between components in these novel crystalline solid forms may differ without consequence to either the novelty of the crystalline solid forms, or the data that is disclosed for, and relevant to, each of the crystalline solid forms, disclosed herein.

A "therapeutically effective amount" of an active pharmaceutical ingredient with respect to the methods of the invention relating to treatment, prevention, or reducing the severity of a viral infection refers to an amount of the active pharmaceutical ingredient in a preparation which, when administered as part of a desired dosage regimen to a subject (preferably a human), alleviates a symptom, ameliorates a condition, or slows the onset of disease conditions for the type of infection or virus specified, according to clinically acceptable standards for the disorder or condition to be treated at a reasonable benefit/risk ratio.

"Percent" or "%" as used herein expresses the number of parts per 100. Where percent or % is used with regard to concentration or weight, it refers to the number of parts of the particular ingredient in a total of 100 parts weight or volume. For example, a product expressed as 0.3% w/v means 0.3 gm in 100 mL. A product expressed as 10% w/w is interpreted as 10 gm in 100 gm. A 0.05% w/v API solution means that 100 ml of the product contains 0.05 g of API. In another example, 0.1% w/w API means there is 0.1 gm of API in every 100 gm of product.

As used in the specification and the appended claims, the singular forms "a," "an," and "the" include singular and plural unless the context dictates otherwise. Thus, "a", "an" or "the", means one or more, unless specified otherwise.

The term "about" as used herein means approximately ±5% of the value. When the term "about" is used in conjunction with a numerical value or range, it modifies that value or range by extending the boundaries above and below the numerical values set forth. In general, the term "about" is used herein to modify a numerical value above and below the stated value by a variance of 5 percent, up or down (higher or lower), i.e., ±5%, unless a different variance is indicated (e.g., ±30%, ±20%, ±15%, ±10%, ±3%, ±2%, ±1%, ±0.5% etc.).

As used herein, "and/or" refers to and encompasses each of the listed items individually, as well as any and all possible combinations of one or more of the listed items.

When the term "in" or "into" is used in the specification or the claims, it is intended to additionally mean "on" or "onto."

When the term "includes" or "including" is used in the specification or the claims, it is intended to be inclusive in a manner similar to the term "comprising" as that term is interpreted when employed as a transitional word in a claim.

As used herein, the terms "optional" and "optionally" mean that the subsequently described circumstance may or may not occur, so that the description includes instances where the circumstance occurs and instances where it does not.

Where features or aspects of the disclosure or claims are described in terms of Markush groups, those skilled in the art will recognize that the disclosure is also thereby described in terms of any individual member or subgroup of members of the Markush group.

In addition, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 members refers to groups having 1, 2, or 3 members. Similarly, a group having 1-5 members refers to groups having 1, 2, 3, 4, or 5 members, and so forth.

EXAMPLES

The disclosure is further illustrated by the following examples which are provided merely to be exemplary and do not limit the scope of the invention. Certain modifications and equivalents will be apparent to those skilled in the art and are intended to be included within the scope of the disclosure. The present disclosure provides, but is not limited to, the following formulation examples.

Example 1

A study was performed in rats with formulations A and B, and a control formulation. Formulation A was IMQ+penetration enhancer (P.E.) at 20 μg/100 μL. Formulation B was IMQ-Fe+P.E. at 20 μg/100 μL. The Control formulation was IMQ at 20 μg/100 μL in ethanol. Formulations A and B and the Control were each applied to a shaved area of rat skin once daily for 21 days.

After application of the three formulations for 24 hours, there was a significant ($p<0.001$) increase of the serum interferon α and γ in the animals treated with formulations A or B. A significant increase of serum interferon α and γ was also observed after 21 days of daily application of formulations A and B. The increase of interferon α in formulation B was ~40% and ~100% more when compared to the Control (imiquimod in ethanol) after 24 hours and after 21 days.

Imiquimod and IMQ-Fe were found to be effective at a low dose, 20 μg/100 μL. In addition, IMQ-Fe had fast on-site action. Topical absorption of the drug occurred within 5 minutes. Results indicate drug delivery will be faster if administered by nasal spray.

Figure 22:
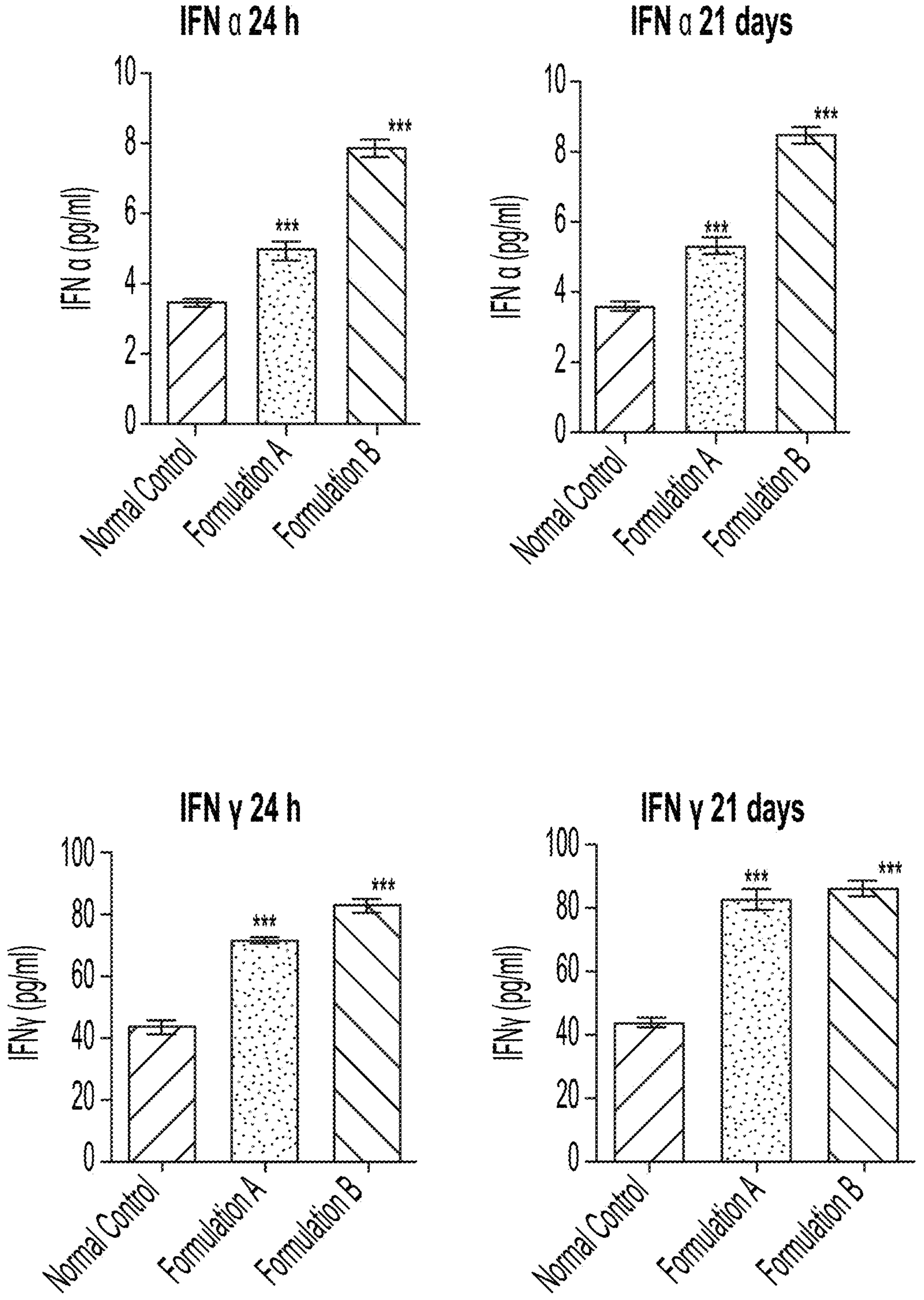
FIG. 22 depicts the effect of Imiquimod and IMQ-Fe Formulations on Serum Interferon α and γ (pg/mL) in rats.

The results are depicted in FIG. 22.

Imiquimod has an established safety profile. It has been approved for marketing in the U.S. (and other countries) as IMQ cream (12.5 mg IMQ/packet). The results indicate that imiquimod, or one of the novel cocrystals discovered by the inventors, such as IMQ-Fe, could be administered as a nasal spray with a much lower drug concentration, 25 μg IMQ-Fe in 50 μl spray, than the topical cream. The excipients used are safe, and imiquimod and ferulic acid are non-irritants.

Example 2 (IMQ-Fe)

IMQ-Fe was prepared by weighing equimolar amounts of imiquimod and ferulic acid (40 mg imiquimod and 32 mg ferulic acid), and then mixing and mechanically grinding them with mortar and pestle for about 30 minutes at room temperature, 19-22° C. Small quantities of methanol were added at regular intervals of time. The total amount of methanol added was 20 ml. The solids (imiquimod and coformer) partially dissolved during grinding, such that they formed a wet powder or paste. During grinding most of the methanol evaporated. The mixture was dried in a vacuum oven at room temperature.

Example 3

Samples of the imiquimod-ferulic acid complex prepared above were evaluated using powder X-ray diffraction (PXRD), thermogravimetric analysis (TGA), and differential scanning calorimetry (DSC).

PXRD is a non-destructive technique widely applied in cocrystal characterization, in which the appearance or disappearance of new peaks in the PXRD patterns, compared to individual components, confirms a change in the crystalline phase and indicates the potential formation of a cocrystal.

A cocrystal should exhibit unique diffraction peaks compared to the individual components of the cocrystal. Unique diffraction peaks indicate a change in the crystalline phase and the formation of a cocrystal. The cocrystal may present lower peak intensity than the individual components, indicating a less crystalline material. This can be corroborated with DSC. Such a result could also relate to a reduction in particle size.

PXRD was performed on a sample of the imiquimod-ferulic acid complex. The powder samples were exposed to Cu-Kα radiation (40 kV and 40 mA) using a diffractometer (D8 ADVANCE; Bruker AXS, Madison, WI, USA) over an angular range of 5-40° 2θ with a step size of 0.0196° and a dwell time of 0.5 s. Data analysis was performed using commercially available software (JADE Materials Data, Inc., Livermore, CA).

The PXRD pattern of a complex prepared according to Example 2 is shown in FIG. 1. The pattern shows characteristic peaks with 2θ values at: 12.3, 13.3, 15.1, 17.2, 17.7, 17.9, 18.7, 19.5, 19.9, 23.5, 24.7, 25.7, 26.9, 27.5, 28.1, 28.9, 29.5, 30.4 and 31.5°. This PXRD pattern has characteristic peaks that appear only in the sample prepared with imiquimod and ferulic acid and are not found in the PXRD patterns for imiquimod or ferulic acid. Crystalline imiquimod has characteristic peaks with 2θ values of 11, 15, 19, 22 and 24°. [Reference: patent CA2551616A1]. Crystalline ferulic acid has characteristic peaks with 2θ values of 9, 10, 13, 16, 18, 22, 24, 26, 29, and 32° [Reference: Rezaei et al., Improving the solubility and in vitro cytotoxicity (anticancer activity) of ferulic acid by loading it into cyclodextrin nanosponges, 2019]. The appearance and disappearance of new peaks in the PXRD pattern in the imiquimod-ferulic acid complex, compared to the patterns of the individual components (imiquimod and ferulic acid), confirms a change in the crystalline structure and indicates the formation of a new cocrystal.

Figure 2:
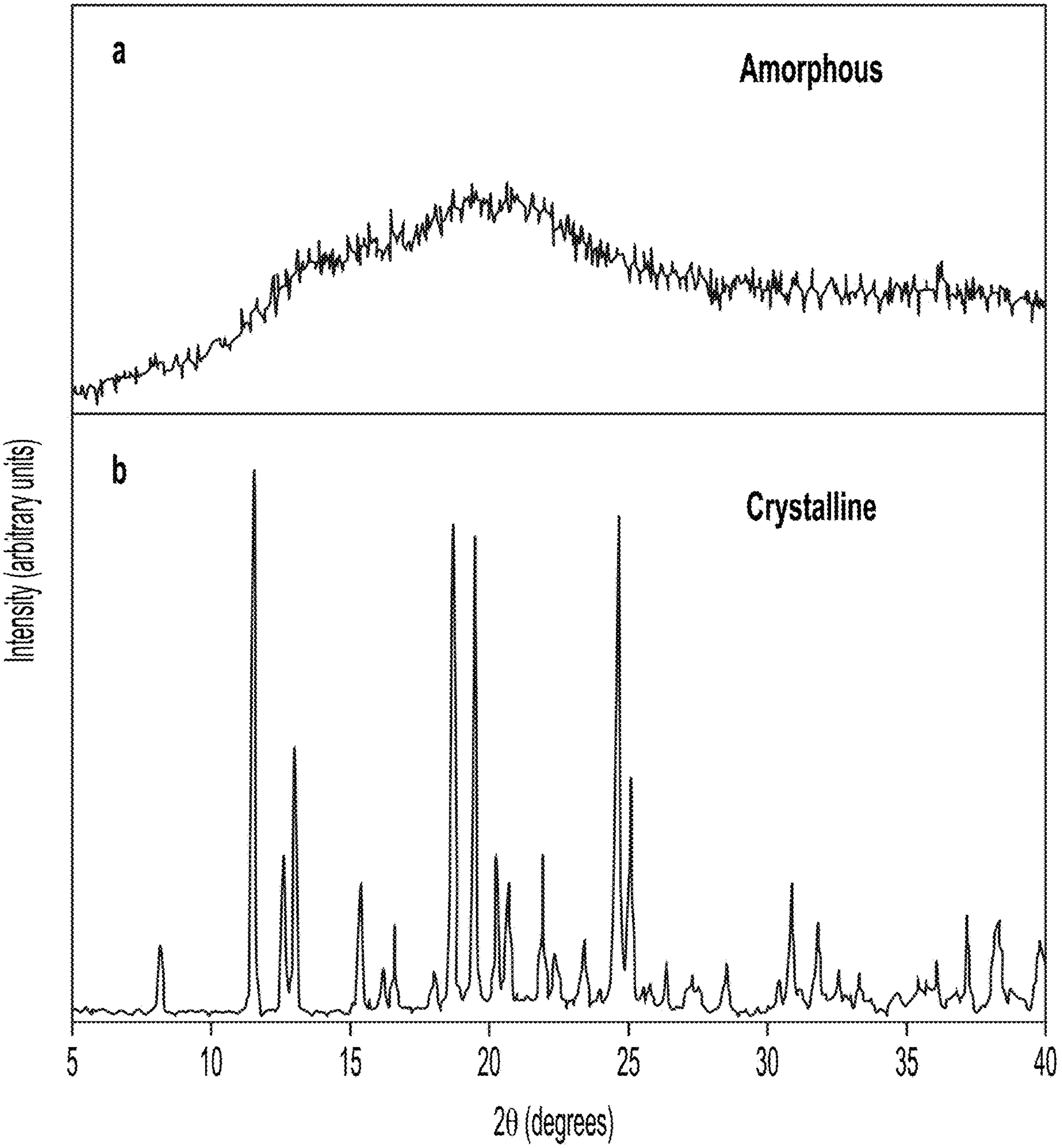
FIG. 2 is a comparison of the PXRD pattern of an amorphous substance to the PXRD pattern of the crystalline substance.

Moreover, the PXRD pattern in FIG. 1 demonstrates that the sample was crystalline. FIG. 2 is a comparison of the PXRD pattern of an amorphous substance ((a) top section) to the PXRD pattern of the crystalline substance ((b) in bottom section). The amorphous material has a diffuse X-ray diffraction pattern, rather than having clear high intensity peaks found in the pattern for the crystalline material. The PXRD pattern in FIG. 1 does not have a diffuse X-ray diffraction pattern.

Cocrystals exhibit different physicochemical properties from their individual components. This includes differences between the melting point of the cocrystal and melting points of the individual components of the cocrystal. DSC is a precise technique that can be employed to evaluate the thermal behavior of cocrystals. In most cases, a single melting point is formed at an intermediate temperature compared to the melting points of the individual components.

DSC was used to evaluate the thermal behavior of a sample of the material prepared according to Example 2 (imiquimod and ferulic acid). A differential scanning calorimeter (model Q2000, TA Instruments) equipped with a refrigerated cooling accessory was used to analyze a sample. Between 5 and 10 mg of sample was hermetically sealed in an aluminum pan. All measurements were performed at a heating rate of 10° C./min under nitrogen purge (50 mL/min). The instrument was calibrated with indium.

Figure 3:
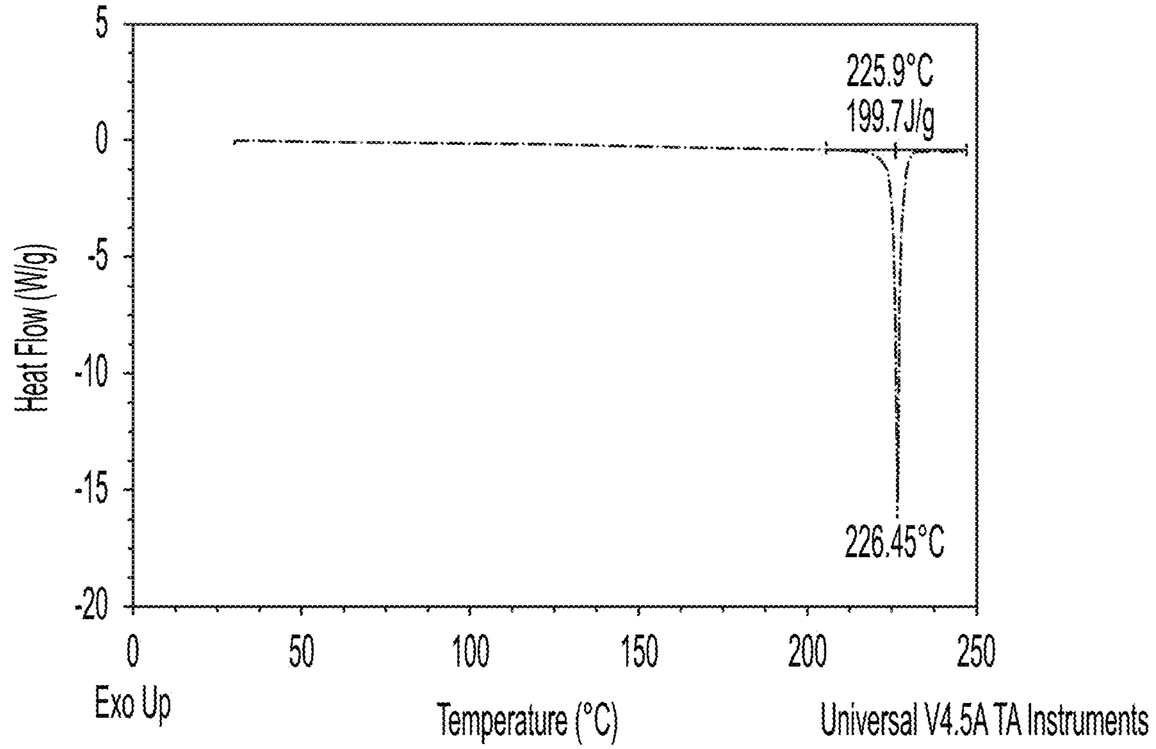
FIG. 3 is the DSC thermogram of the imiquimod-ferulic acid cocrystal IMQ-Fe.

The DSC thermogram is shown in FIG. 3. The complex has a single endotherm at about 225.9-226.45° C. This temperature falls between the melting point of imiquimod, which has a melting point of 292-296° C., and the melting point of ferulic acid, which has a melting point of 168-172° C. (form I ferulic acid Tm=175° C.). This is strong evidence that a cocrystal is formed.

TGA can be used to identify the presence of solvents in a raw material. TGA can also be used to evaluate the thermal stability of a raw material such as a cocrystal. If the material is a hydrate, there will be about 5% water loss up to 98° C. and potential degradation may also occur indicating instability under thermal conditions. If the material is anhydrous, it will be more thermally stable, because it will present a higher melting point and degradation temperature.

TGA was used to evaluate the thermal stability of the imiquimod-ferulic acid complex. In a thermogravimetric analyzer (model Q50 TGA, TA Instruments, New Castle, DE), 5-10 mg of sample was heated in an aluminum pan from RT to up the melting point of the cocrystal at 10° C./min under dry nitrogen purge (50 mL/min). The TGA data were analyzed using commercial software (Universal Analysis 2000, TA Instruments, New Castle, DE).

Figure 4:
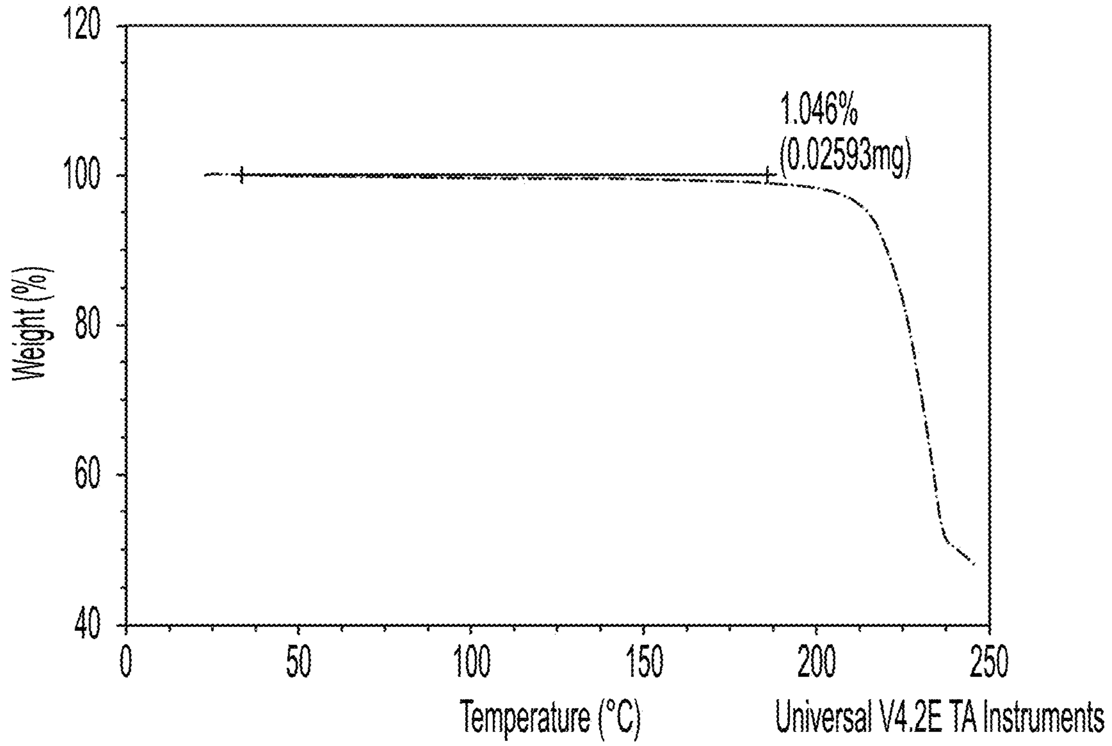
FIG. 4 is the TGA curve of the imiquimod-ferulic acid cocrystal IMQ-Fe.

As shown in FIG. 4, a single endotherm around the cocrystal melting point appeared. The curve also indicates that the cocrystal is stable up to 180° C. with negligible weight loss, which indicates that this cocrystal is anhydrous.

If it were a monohydrate, it would have had a water loss around 98° C. and potential degradation loss after that point.

The data generated by PXRD, DSC and TGA confirms that the newly formed imiquimod-ferulic acid complex is a cocrystal. We have designated this new compound IMQ-Fe.

Example 4

FTIR spectroscopy was used to confirm cocrystal formation of imiquimod and ferulic acid. The IR Spectras of Imiquimod and cocrystals (Vertex 70, Bruker, Ettlingen, Germany; equipped with a globar mid-IR source) were obtained using an attenuated total reflectance (ATR) accessory (single reflection germanium crystal) and a DLaTGS detector. The resolution was 4 $cm^{-1}$, and 64 scans were acquired in the range of 4000-400 $cm^{-1}$. The peak positions were determined using OPUS software peak picking function.

FTIR, which can be used for the simultaneous study of the spectra of the cocrystals' individual components and of their final mixture with polymer matrices, etc., is an important tool in detecting cocrystal formation and in the elucidation of their structures. The cocrystal provides a different spectrum from that of the components' mixture due to the presence of hydrogen bonds, especially when a carboxylic acid is used as a coformer and when a neutral hydrogen bond O—H _ _ _ N is formed between an acid and a base. Clear IR spectra differences are observed between a neutral carboxylic acid functional group and a carboxylic anion. Neutral carboxylate (—COOH) shows a strong tension band of C═O at about 1700 cm).

The following samples were analyzed by FTIR:

TABLE 1

| Sample No. | Sample Name | Description |
|---|---|---|
| 1 | Imiquimod | |
| 2 | Ferulic acid | |
| 3 | IMQ-Fe | 20 mg IMQ + 16 mg Fe in 50 ml ethanol, the materials dissolved and ethanol was allowed to evaporate at RT |
| 4 | IMQ-Fe ethanol trituration | 40 mg IMQ + 82 mg Fe + 20 mg ethanol, the dispersion was triturated (grinding) and ethanol was allowed to evaporate while triturating |

Figure 5:
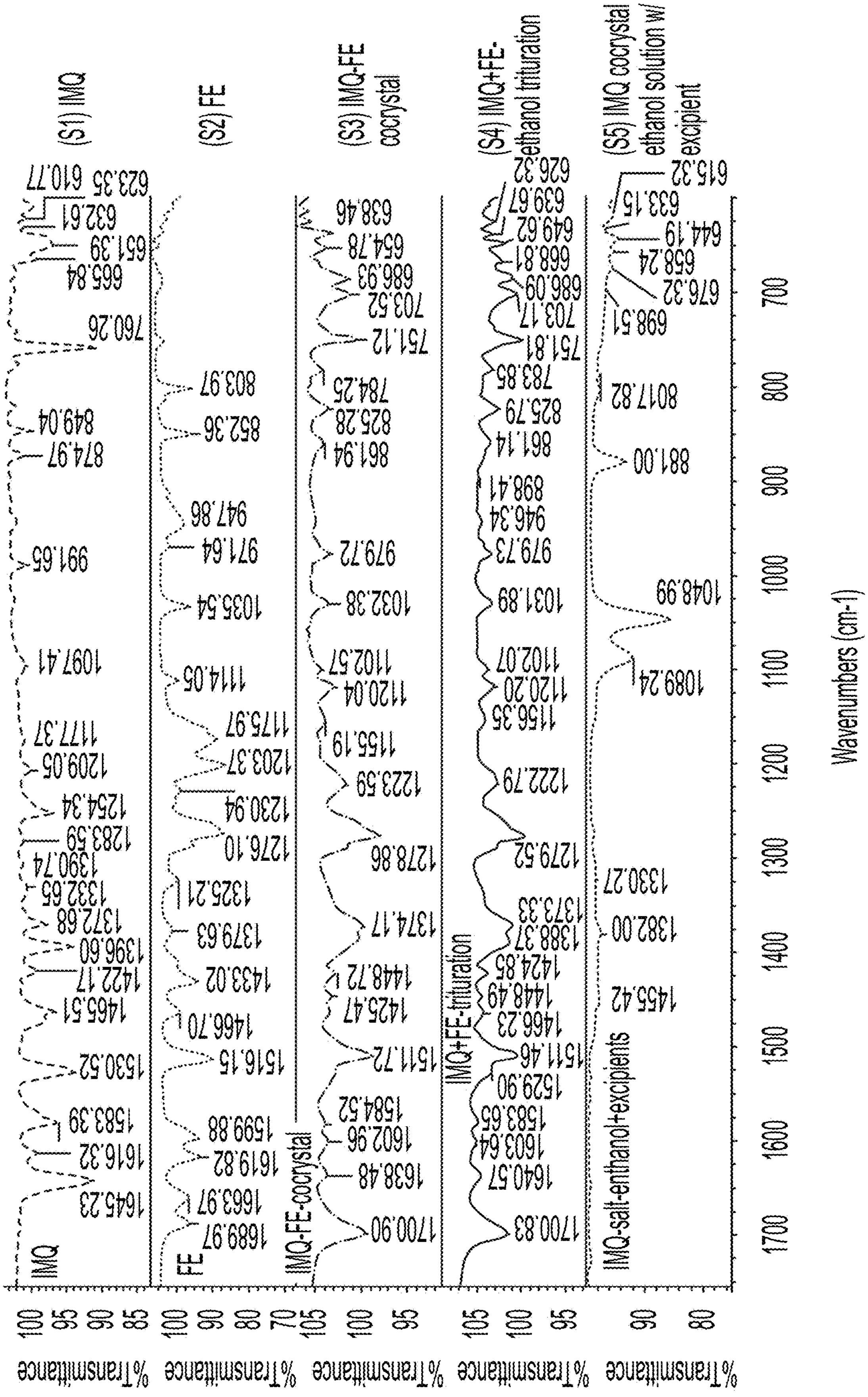
FIG. 5 provides a comparison of the FT-IR spectra over the wavelength range of 1700-600 $cm^{-1}$ of imiquimod, ferulic acid, IMQ-Fe, IMQ-ferulic acid cocrystal made by ethanol trituration, and imiquimod-ferulic acid cocrystal made in an ethanol solution with an excipient.

FIG. 5 shows a comparison of IR spectra for samples 1-4 over the wavelength range of 1700-600 $cm^{-1}$.

Figure 6:
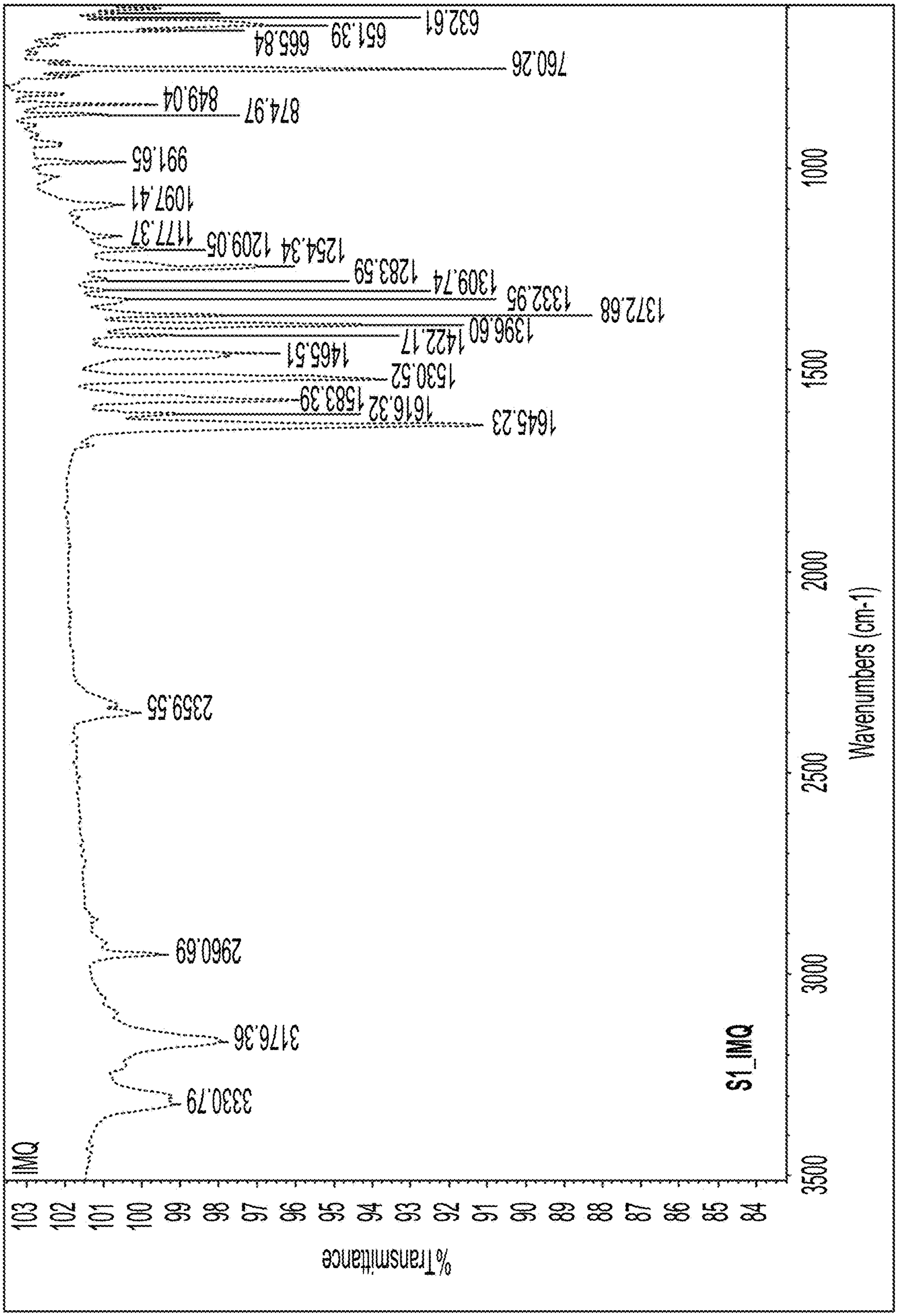
FIG. 6 is an IR spectrum of imiquimod, over the wavelength range of 3400-600 $cm^{-1}$.

FIG. 6 is an IR spectrum of imiquimod (Sample 1), over the wavelength range of 3400-600 $cm^{-1}$.

Figure 7:
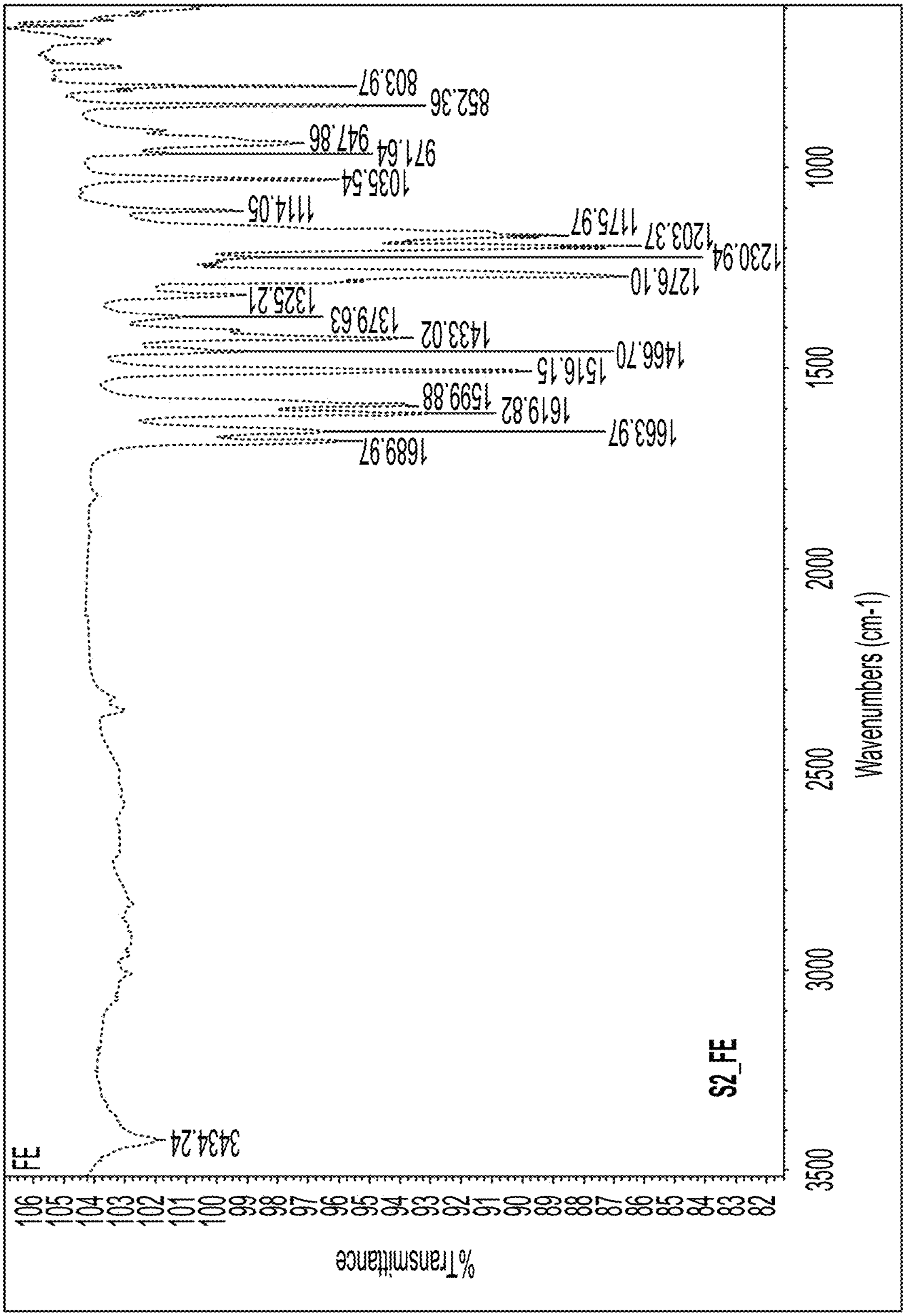
FIG. 7 is an IR spectrum of ferulic acid, over the wavelength range of 3400-600 $cm^{-1}$.

FIG. 7 is an IR spectrum of ferulic acid (Sample 2), over the wavelength range of 3400-600 $cm^{-1}$.

Figure 8:
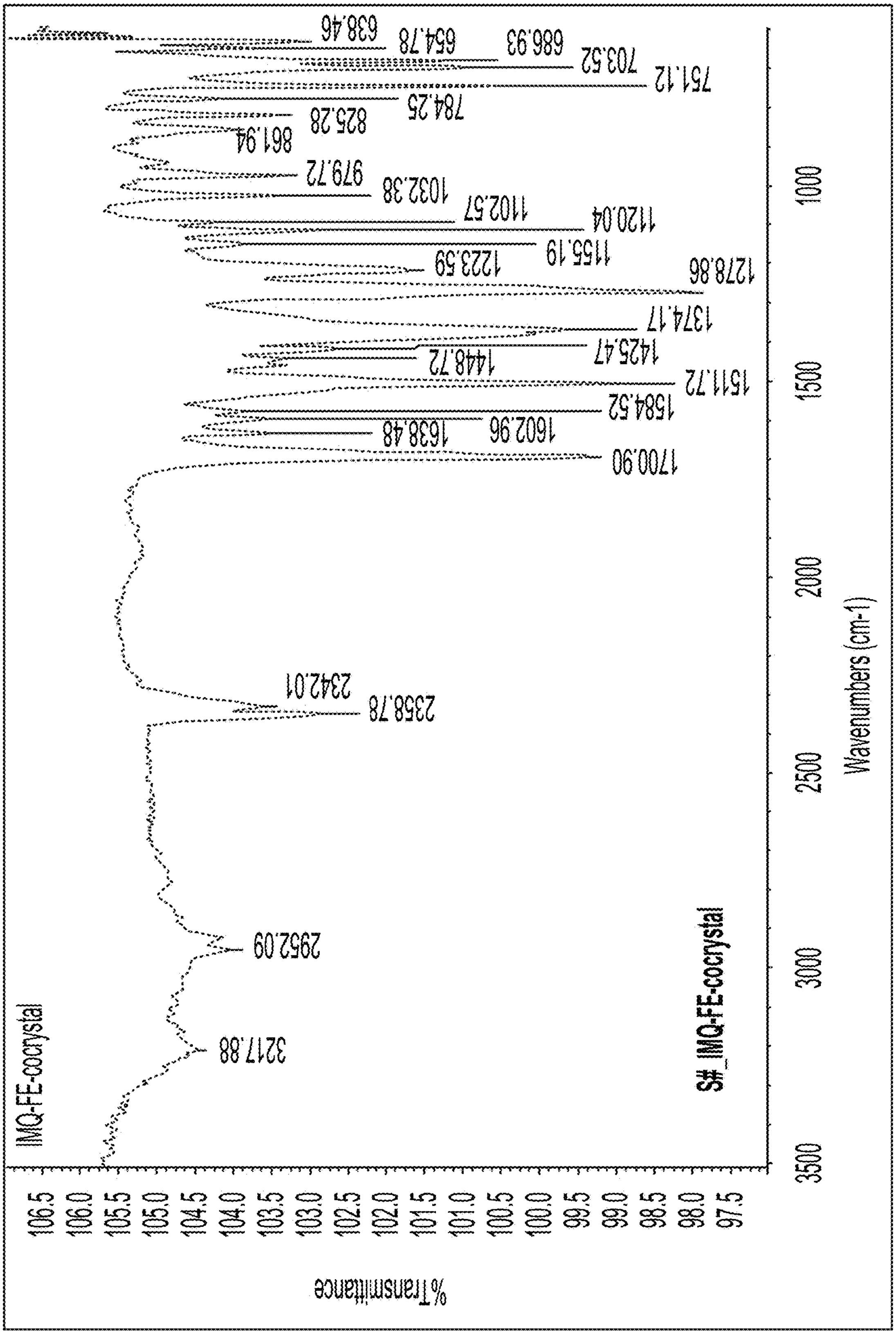
FIG. 8 is an IR spectrum of IMQ-Fe, over the wavelength range of 3400-600 $cm^{-1}$.

FIG. 8 is an IR spectrum of IMQ-Fe (Sample 3), over the wavelength range of 3400-600 $cm^{-1}$.

Figure 9:
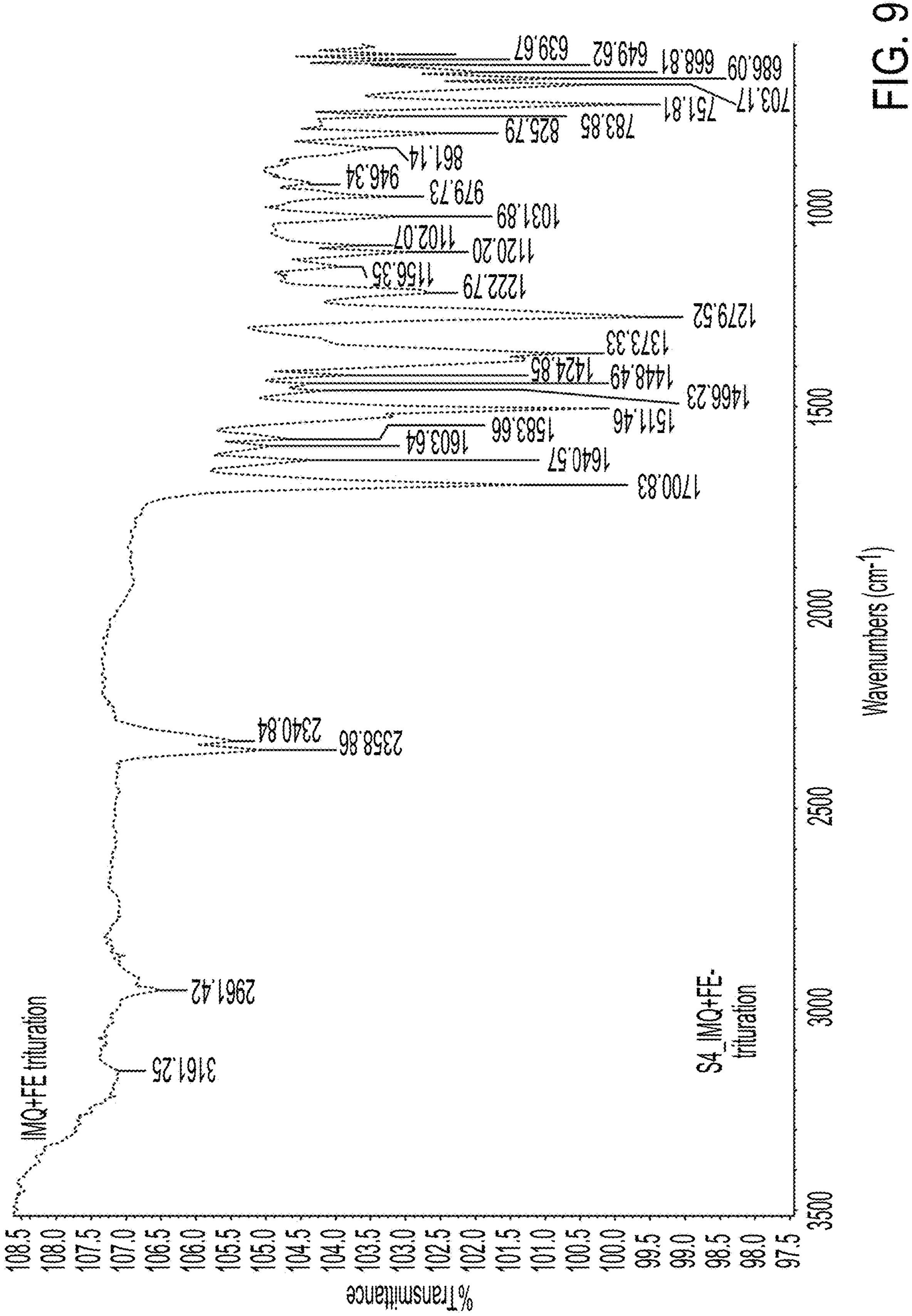
FIG. 9 is an IR spectrum of IMQ-Fe made by ethanol trituration, over the wavelength range of 3400-600 $cm^{-1}$.

FIG. 9 is an IR spectrum of IMQ-Fe—ethanol trituration, over the wavelength range of 3400-600 $cm^{-1}$.

If a salt forms, the wavenumbers of carboxylic acid groups at 1689 and 1663 $cm^{-1}$ (free and cyclic carboxylic acid, respectively) should decrease to the lower region around 1580-1620 $cm^{-1}$. However, for the imiquimod-ferulic acid complex, instead of decreasing, the new peak of carboxylic acid shifted to higher wavenumbers around 1700.90 $cm^{-1}$. This indicates that a cocrystal was formed rather than a salt. With regard to the samples for ethanol trituration, and ethanol solution with excipient, the peaks for ethanol and excipients may cover the characteristic peaks of imiquimod and ferulic acid when dissolved.

The IR data for samples 3 and 4 indicates that either method of preparation produces the same cocrystal. However, the morphology of the two samples appears to be different.

Example 5 (IMQ-Ac)

IMQ-Ac was prepared by weighing equimolar amounts of imiquimod and acetic acid (0.2 mg imiquimod and 60.5 mg acetic acid) in 10 ml methanol, and then mixing and mechanically grinding them with mortar and pestle for up to 30 minutes at room temperature, 19-22° C. Small quantities of methanol were added at regular intervals of time. The solids (imiquimod and coformer) partially dissolved during grinding, such that they formed a wet powder or paste. During grinding most of the methanol evaporated. The mixture was dried in a vacuum oven at room temperature.

Samples of this imiquimod-acetic acid complex were evaluated using PXRD, TGA, and DSC, according to the protocols described in Example 3.

Figure 10:
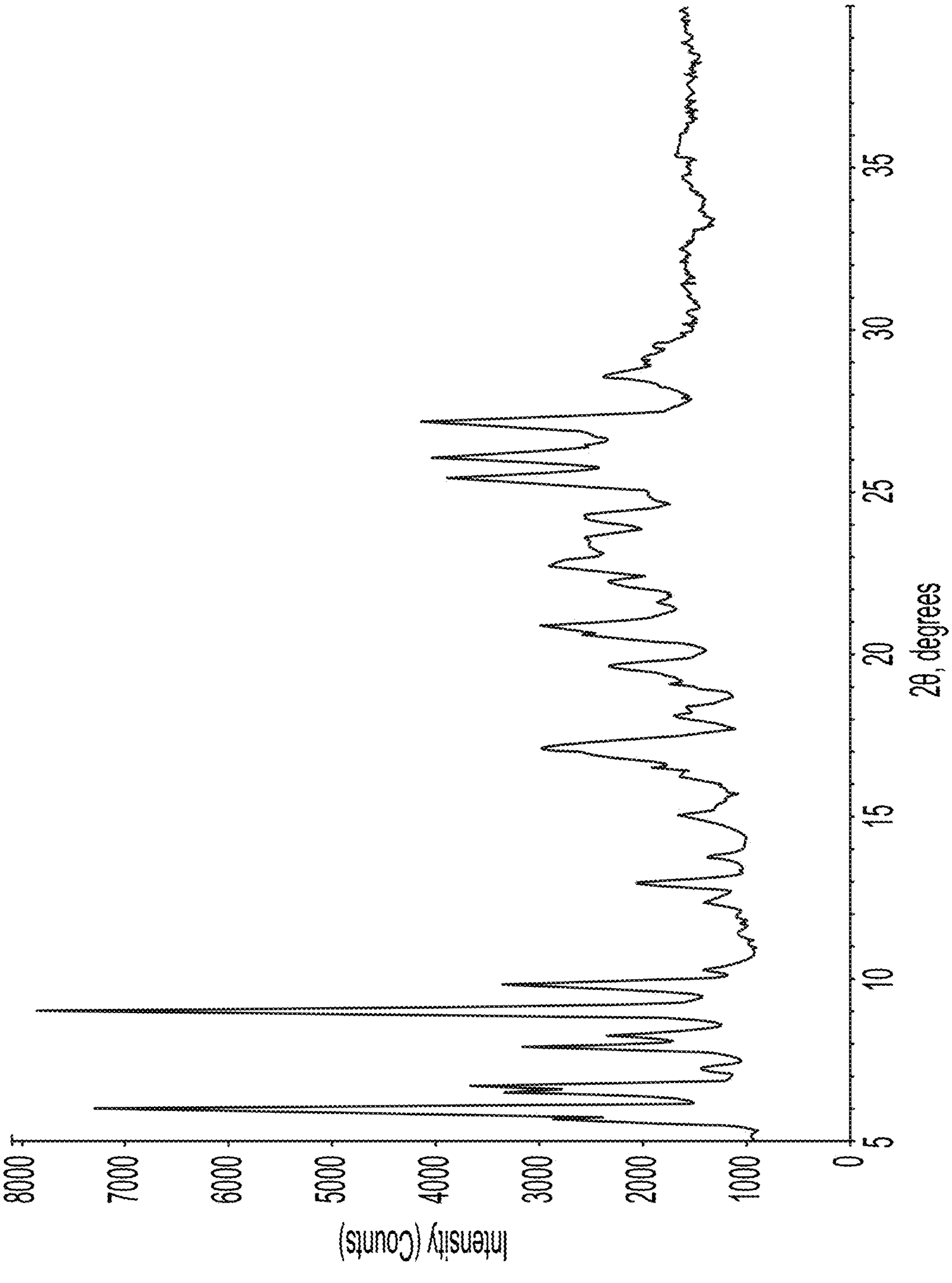
FIG. 10 is the PXRD pattern of the Imiquimod-acetic acid cocrystal IMQ-Ac.

The PXRD pattern of the complex is shown in FIG. 10. The pattern shows characteristic peaks with 2θ values at: 5.9, 6.7, 7.9, 9.0, 9.8, 12.9, 17.1, 20.8, 22.7, 25.5, 26.1 and 27.1°. Crystalline imiquimod has characteristic peaks with 2θ values of 11, 15, 19, 22 and 24°. [Reference: patent CA2551616A1]. Crystalline acetic acid has characteristic peaks with 2θ values of 110, 200, 210, and 311°. The PXRD pattern shown in FIG. 10 has characteristic peaks that appear only in the imiquimod-acetic acid complex, and are not found in the PXRD patterns for imiquimod or acetic acid. The appearance and disappearance of new peaks in the PXRD pattern of the complex, compared to the patterns for the individual components imiquimod and acetic acid, confirmed a change in the crystalline structure and indicate the formation of a new cocrystal. Moreover, the PXRD pattern in FIG. 10 demonstrates that the complex was crystalline.

Figure 11:
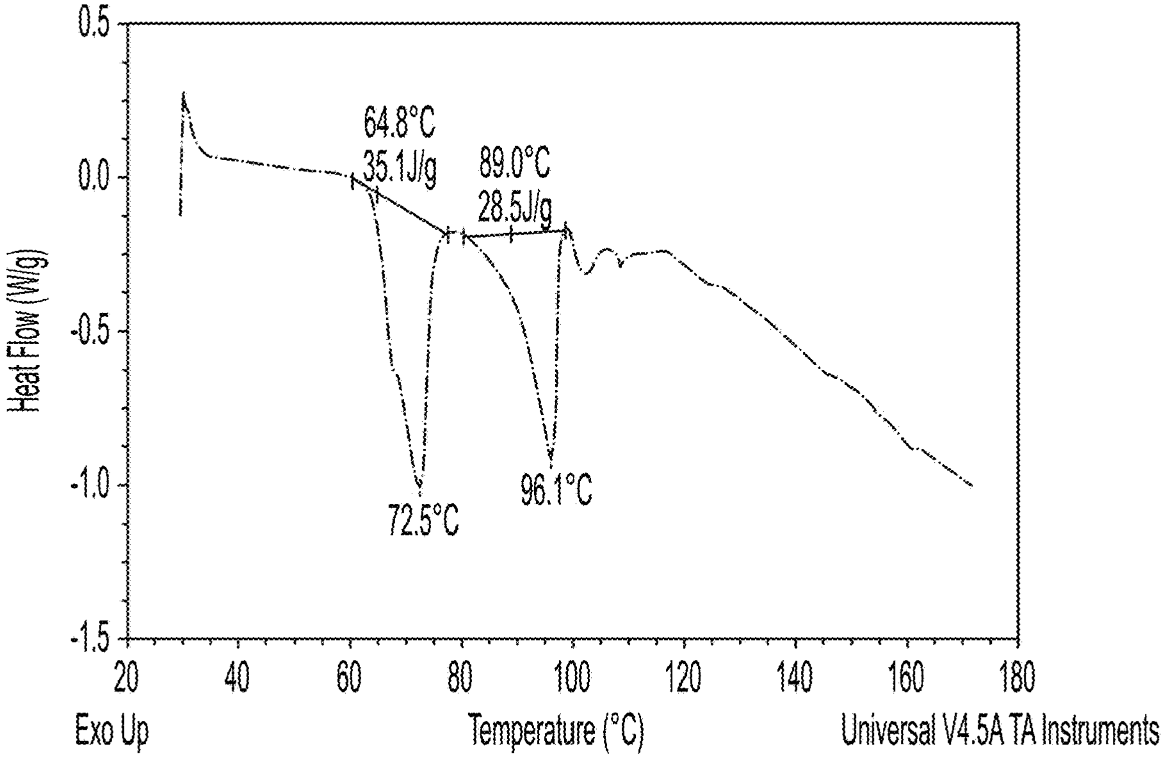
FIG. 11 is the DSC thermogram of the Imiquimod-acetic acid cocrystal IMQ-Ac.

DSC was used to evaluate the thermal behavior of a sample of the imiquimod-acetic acid complex. The DSC thermogram is shown in FIG. 11. The material has complex endotherms at about 64.8-72.5° C. and about 89.0-96.1° C. These temperatures fall between the melting point of imiquimod, which has a melting point of 292-296° C., and the melting point of acetic acid, which has a melting point of 16.6° C. This is strong evidence that a cocrystal is formed.

Figure 12:
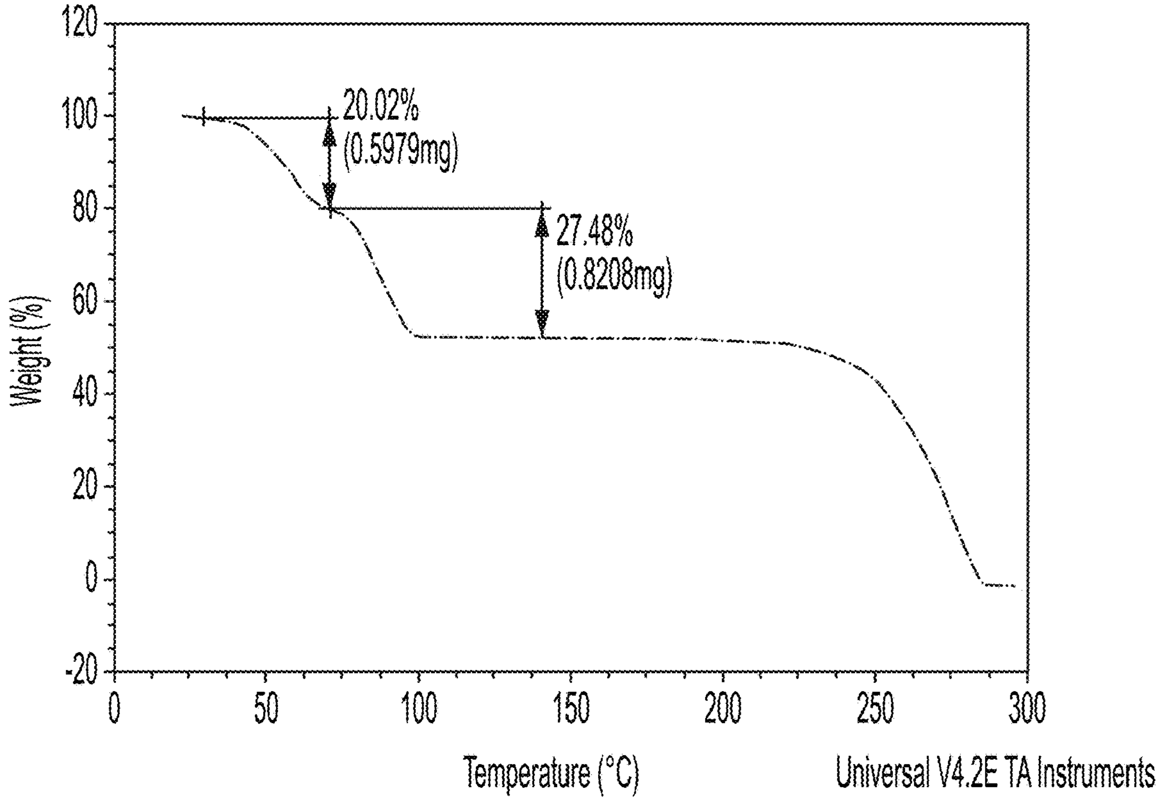
FIG. 12 is the TGA curve of the Imiquimod-acetic acid cocrystal IMQ-Ac.

TGA was used to evaluate the thermal stability of the complex. As shown in FIG. 12, two endotherms around the complex melting point appeared. The first endotherm may be a desolvation/dehydration event, which means that this cocrystal could be a hydrate or methanol solvate cocrystal.

The data generated by PXRD, DSC and TGA confirms that the newly formed imiquimod-acetic acid complex is a cocrystal. We have designated this new compound IMQ-Ac.

Example 6 (IMQ-Co)

IMQ-Co was prepared by weighing equimolar amounts of imiquimod and coumaric acid and then mixing and mechanically grinding them with mortar and pestle for up to 30 minutes, at room temperature, 19-22° C. Small quantities of methanol were added at regular intervals of time. The solids (imiquimod and coformer) partially dissolved during grinding, such that they formed a wet powder or paste. During grinding most of the methanol evaporated. The mixture was dried in a vacuum oven at room temperature.

Samples of this imiquimod-coumaric acid complex were evaluated using PXRD, TGA, and DSC, according to the protocols described in Example 3.

Figure 13:
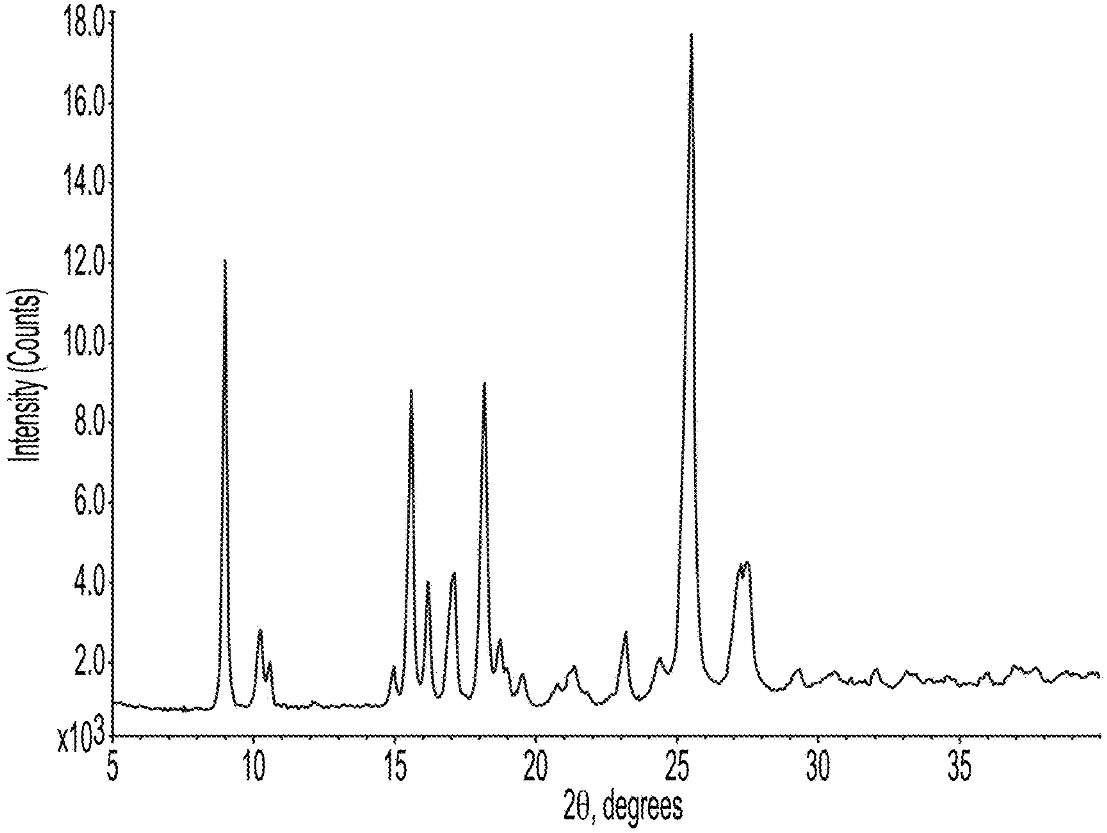
FIG. 13 is the PXRD pattern of the Imiquimod-coumaric acid cocrystal IMQ-Co.

The PXRD pattern of the complex is shown in FIG. 13. The pattern shows characteristic peaks with 2θ values at: 9.0, 10.2, 15.6, 16.2, 18.2, 23.2, 25.5 and 27.5°. Crystalline imiquimod has characteristic peaks with 2θ values of 11, 15, 19, 22 and 24°. [Reference: patent CA2551616A1]. Crystalline coumaric acid has characteristic peaks with 2θ values of 17.5, 19.8, 25.0, and 30.5°. The PXRD pattern shown in FIG. 13 has characteristic peaks that appear only in the imiquimod-coumaric acid complex and are not found in the PXRD patterns for imiquimod or coumaric acid. The appearance and disappearance of new peaks in the PXRD pattern in this complex compared to the patterns for the individual components imiquimod and coumaric acid, confirmed a change in the crystalline structure and indicate the formation of a new cocrystal. Moreover, the PXRD pattern in FIG. 13 demonstrates that the sample was crystalline.

Figure 14:
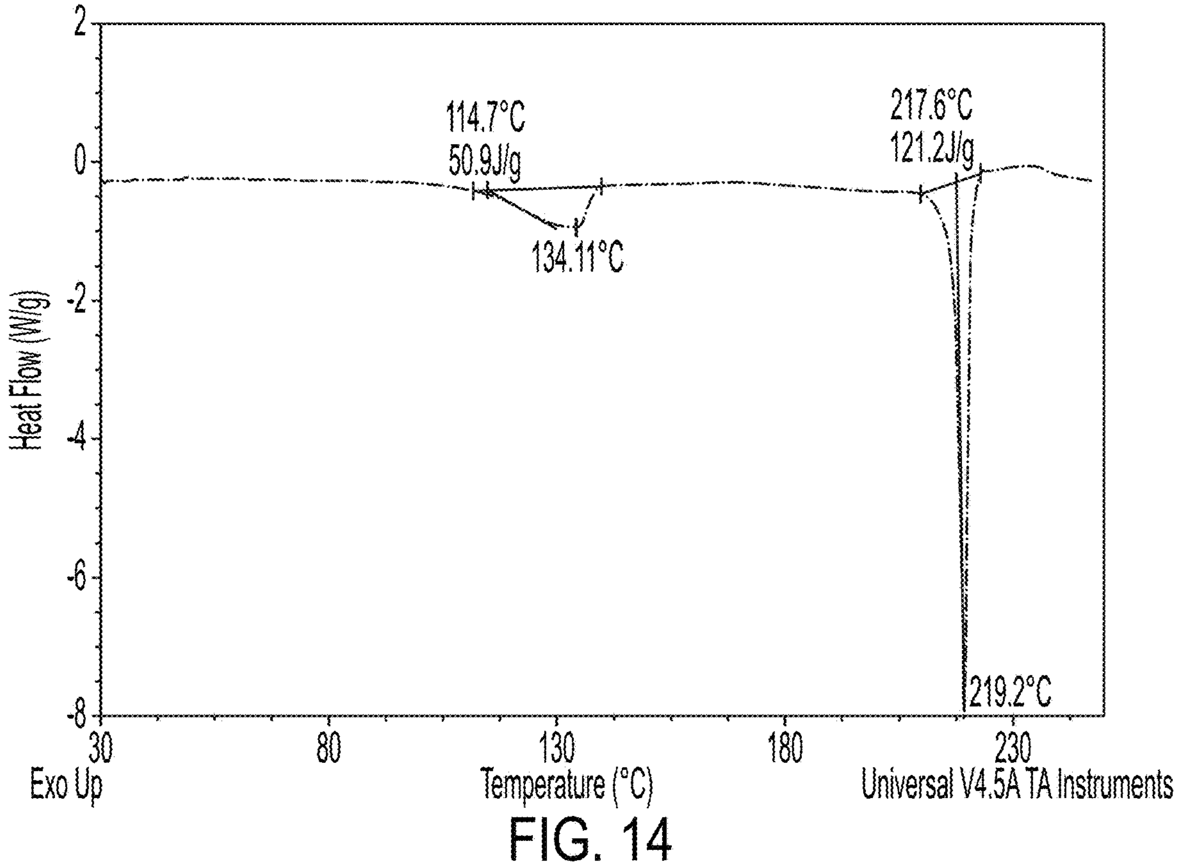
FIG. 14 is the DSC thermogram of the Imiquimod-coumaric acid cocrystal IMQ-Co.

DSC was used to evaluate the thermal behavior of the imiquimod-coumaric acid complex. The DSC thermogram is shown in FIG. 14. The material exhibited complex endotherms. It has two endotherms at about 114.7-134.11° C. and about 217.6-219.2° C. The first endotherm may be attributed to dehydration/desolvation and the second endotherm to the melting point, which suggests this could be a hydrate or methanol solvate cocrystal. The second endotherm falls between the melting point of imiquimod, which has a melting point of 292-296° C., and the melting point of p-coumaric acid, which is 210-213° C.

Figure 15:
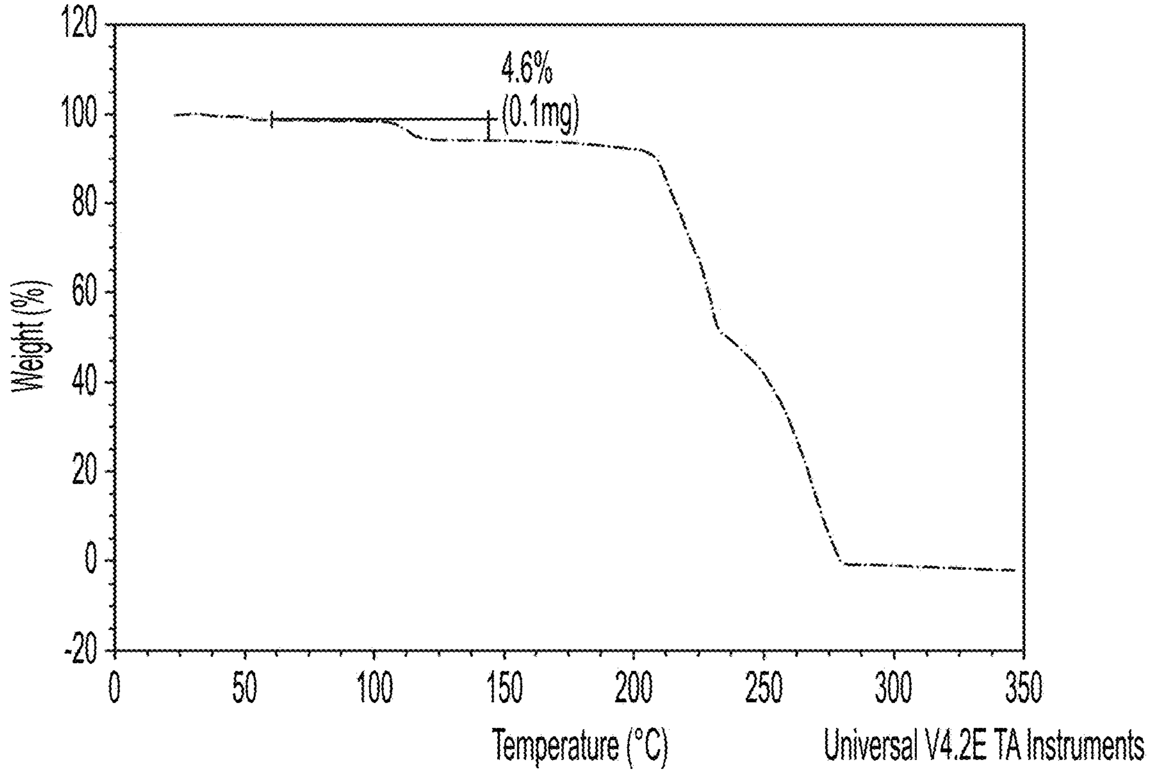
FIG. 15 is the TGA curve of the Imiquimod-coumaric acid cocrystal IMQ-Co.

TGA was used to evaluate the thermal stability of the sample. As shown in FIG. 15, one endotherm around the cocrystal melting point appeared. There was a 4.6% loss of water at about 150° C., indicating that this is a hydrate.

The data generated by PXRD, DSC and TGA confirms that the newly formed imiquimod-coumaric acid complex is a cocrystal. We have designated this new compound IMQ-Co.

Example 7 (IMQ-Ci)

IMQ-Ci was prepared by weighing amounts of imiquimod and citric acid to prepare a 2:1 molar mixture, and then mechanically grinding them with mortar and pestle for up to 30 minutes at room temperature, 19-22° C. Small quantities of methanol were added at regular intervals of time. The solids (imiquimod and coformer) partially dissolved during grinding, such that they formed a wet powder or paste. During grinding most of the methanol evaporated. The mixture was dried in a vacuum oven at room temperature.

Samples of this imiquimod-citric acid complex were evaluated using PXRD, TGA, and DSC, according to the protocols described in Example 3.

Figure 16:
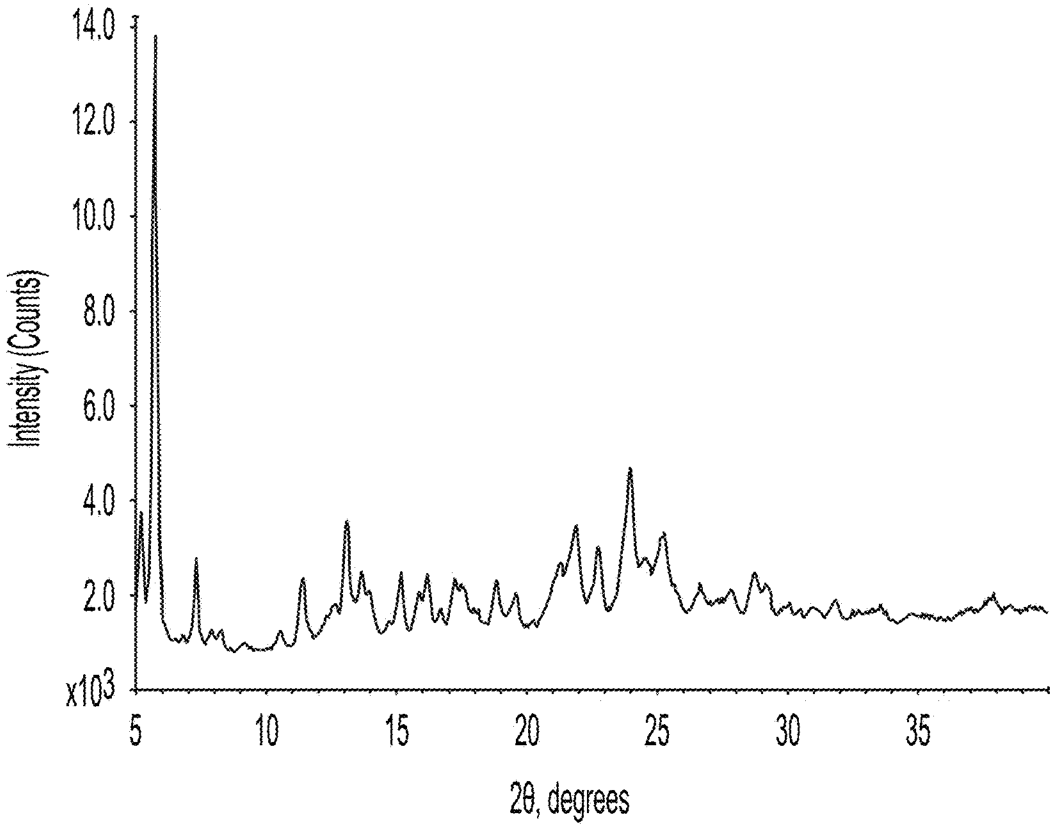
FIG. 16 is the PXRD pattern of the Imiquimod-citric acid cocrystal IMQ-Ci.

The PXRD pattern of this complex is shown in FIG. 16. The pattern shows characteristic peaks with 2θ values at: 5.2, 5.8, 7.3, 13.1, 13.7, 15.2, 21.9, 22.7, 23.4 and 25.3°. Crystalline imiquimod has characteristic peaks with 2θ values of 11, 15, 19, 22 and 24°. [Reference: patent CA2551616A1]. Crystalline citric acid has characteristic peaks with 2θ values of 14, 17, 19, 24, 26, and 29°. The PXRD pattern shown in FIG. 16 has characteristic peaks that appear only in the imiquimod-citric acid complex and are not found in the PXRD patterns for imiquimod or citric acid. The appearance and disappearance of new peaks in the PXRD pattern of the imiquimod-citric acid complex compared to the patterns for the individual components imiquimod and citric acid, confirmed a change in the crystalline structure and indicate the formation of a new cocrystal. Moreover, the PXRD pattern in FIG. 16 demonstrates that the sample was crystalline.

Figure 17:
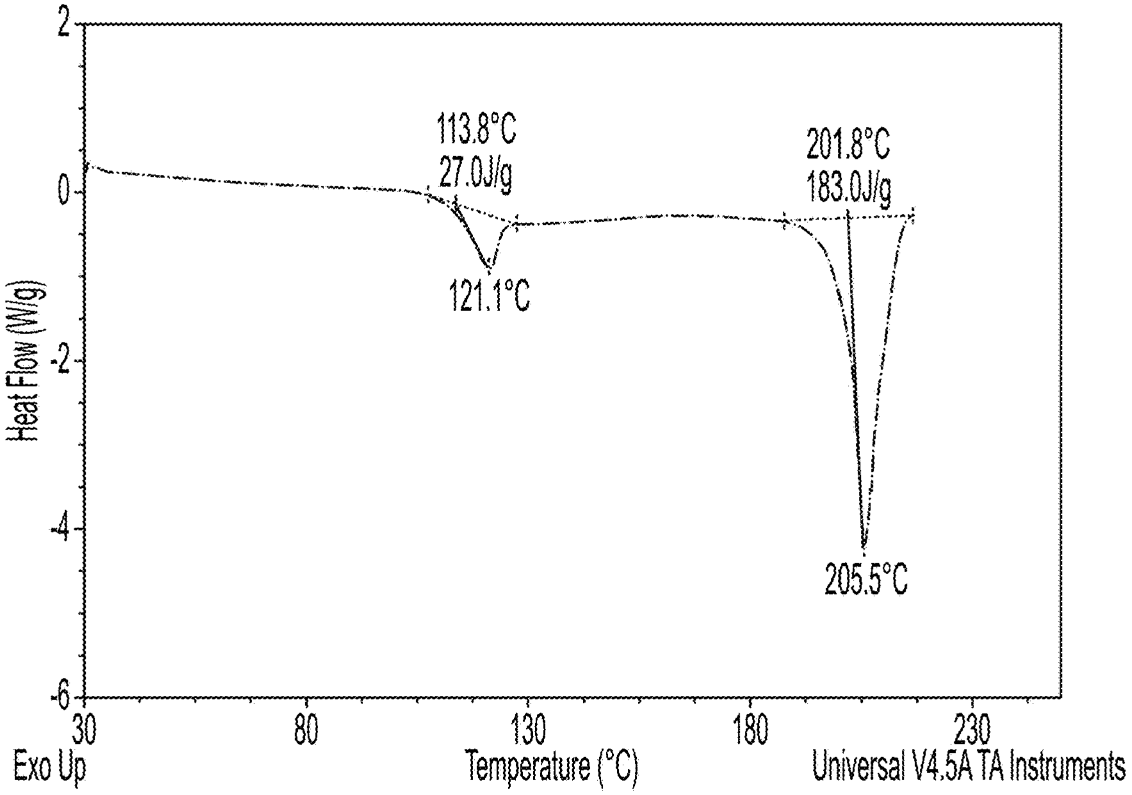
FIG. 17 is the DSC thermogram of the Imiquimod-citric acid cocrystal IMQ-Ci.

DSC was used to evaluate the thermal behavior of the imiquimod-citric acid complex. The DSC thermogram is shown in FIG. 17. The material has two endotherms at about 113.8-121.1° C. and about 201.8-205.5° C. The second endotherm falls between the melting point of imiquimod, which has a melting point of 292-296° C., and the melting point of citric acid, which has a melting point of 153° C. This is strong evidence that a cocrystal is formed.

Figure 18:
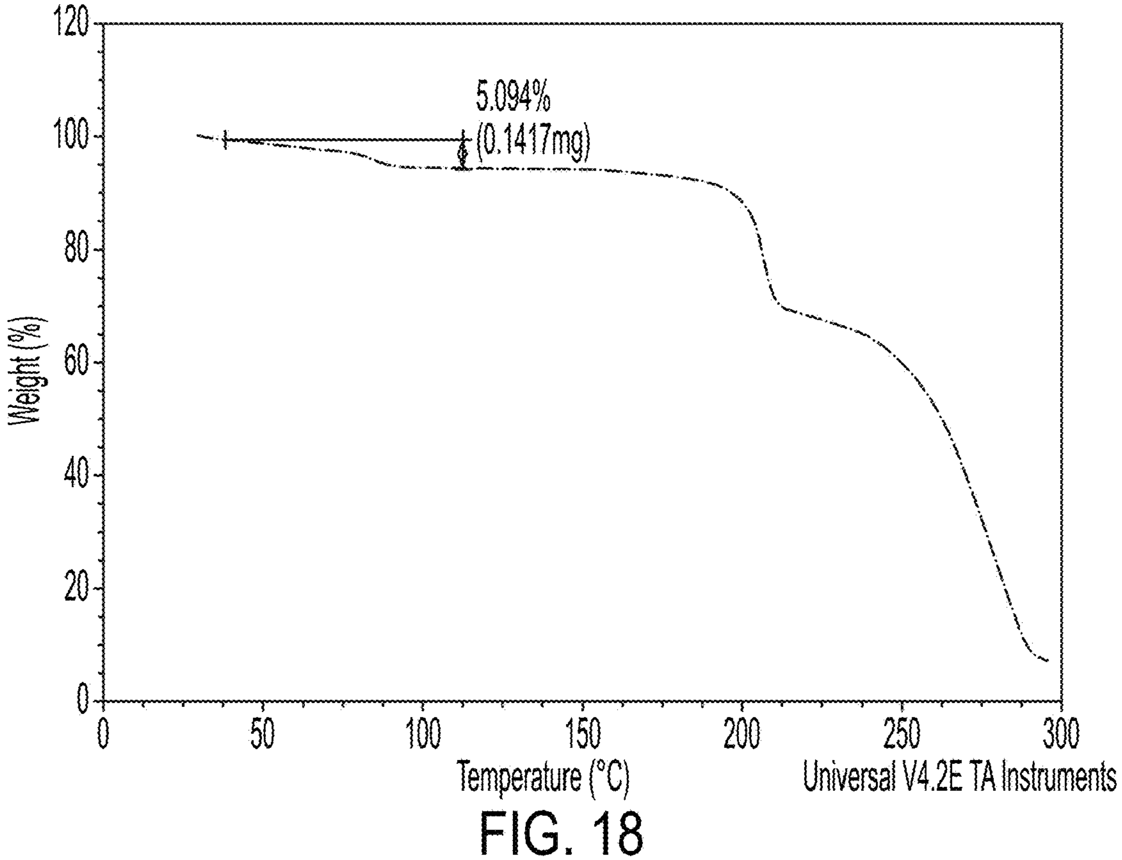
FIG. 18 is the TGA curve of the Imiquimod-citric acid cocrystal IMQ-Ci.

TGA was used to evaluate the thermal stability of the complex. As shown in FIG. 18, two endotherms around the cocrystal melting points appeared. The curve also indicates the crystal is stable until around 180° C.

The first endotherm may be a desolvation/dehydration event, which means that this cocrystal could be a hydrate or methanol solvate cocrystal. There was a 5.0% weight loss at about 120° C., indicating this is a hydrate.

The data generated by PXRD, DSC and TGA confirms that the newly formed imiquimod-citric acid complex is a cocrystal. We have designated this new compound IMQ-Ci.

Example 8 (IMQ-Tar)

IMQ-Tar was prepared by weighing amounts of imiquimod and tartaric acid to prepare a 2:1 molar mixture, and then mechanically grinding the mixture with mortar and pestle for up to 30 minutes at room temperature, 19-22° C. Small quantities of methanol were added at regular intervals of time. The solids (imiquimod and coformer) partially dissolved during grinding, such that they formed a wet powder or paste. During grinding most of the methanol evaporated. The mixture was dried in a vacuum oven at room temperature.

Samples of this imiquimod-tartaric acid complex were evaluated using PXRD, TGA, and DSC, according to the protocols described in Example 3.

Figure 19:
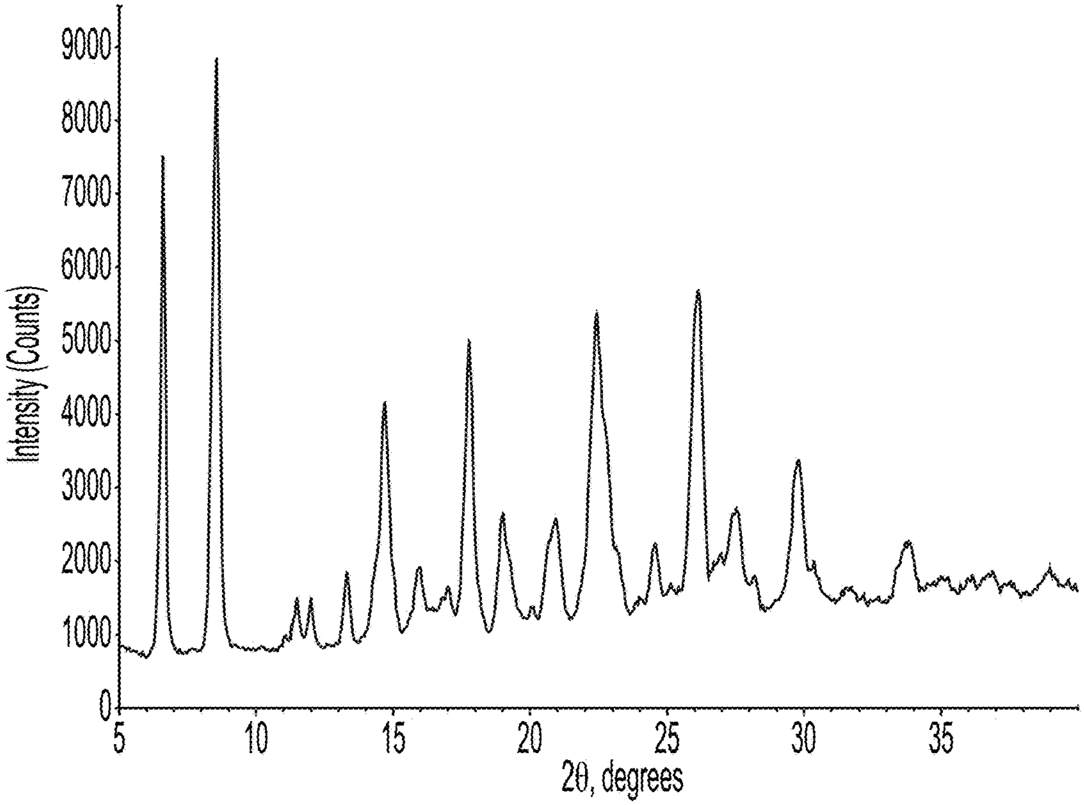
FIG. 19 is the PXRD pattern of the Imiquimod-tartaric acid cocrystal IMQ-Tar.

The PXRD pattern this complex is shown in FIG. 19. The pattern shows characteristic peaks with 2θ values at: 6.6, 8.5, 13.3, 14.7, 17.8, 19.0, 20.9, 22.4, 26.1, 27.5 and 29.8°. Crystalline imiquimod has characteristic peaks with 2θ values of 11, 15, 19, 22 and 24°. [Reference: patent CA2551616A1]. Crystalline tartaric acid has characteristic peaks with 2θ values of 11.5, 20.5, 25, 29 and 36°. The PXRD pattern shown in FIG. 19 has characteristic peaks that appear only in the imiquimod-tartaric acid complex and are not found in the PXRD patterns for imiquimod or tartaric acid. The appearance and disappearance of new peaks in the PXRD pattern for the complex, compared to the patterns for the individual components, imiquimod and tartaric acid, confirmed a change in the crystalline structure and indicate the formation of a new cocrystal. Moreover, the PXRD pattern in FIG. 19 demonstrates that the sample was crystalline DSC was used to evaluate the thermal behavior of the imiquimod-tartaric acid complex. No melting point or endotherm was detected.

Figure 20:
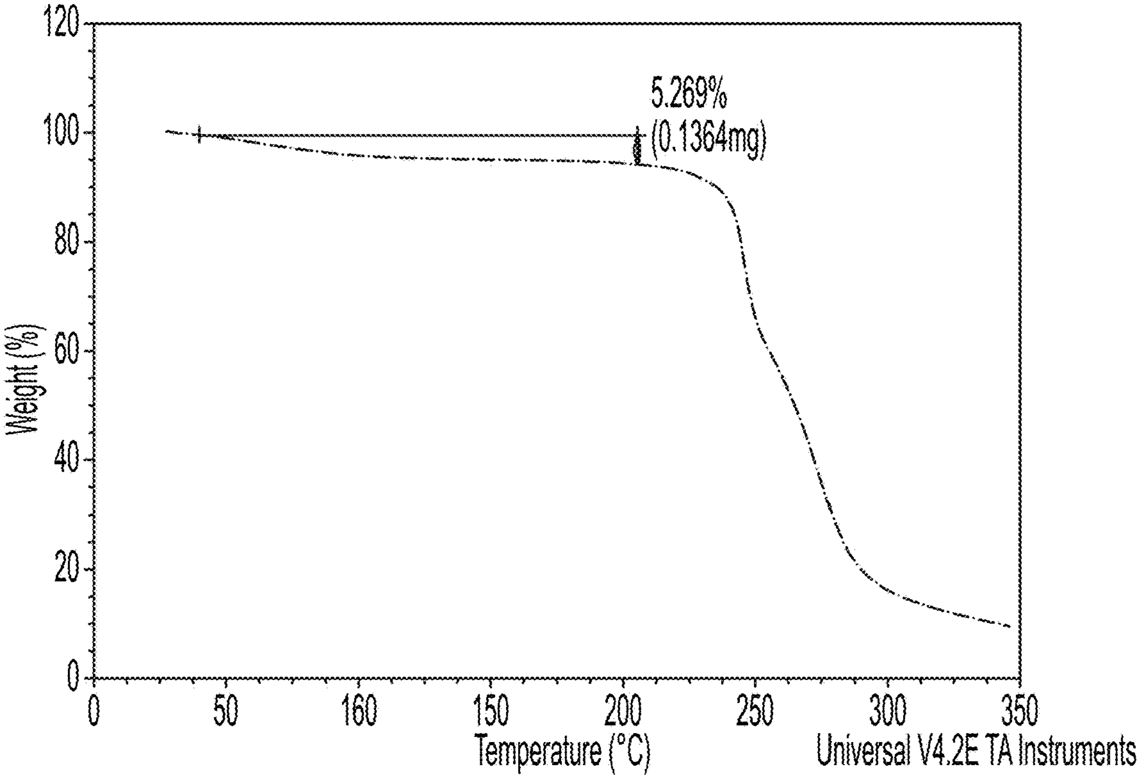
FIG. 20 is the TGA curve of the Imiquimod-tartaric acid cocrystal IMQ-Tar.

TGA was used to evaluate the thermal stability of the sample. As shown in FIG. 20, one endotherm appeared. This endotherm may be a desolvation/dehydration event, which means that this cocrystal could be a hydrate or methanol solvate cocrystal. The curve also indicates the crystal is stable until around 220° C.

The data generated by PXRD, DSC and TGA confirms that the newly formed imiquimod-tartaric acid complex is a cocrystal. We have designated this new compound IMQ-Tar.

Example 9: Solubility of Imiquimod and Imiquimod-Ferulic Acid Cocrystal

Figure 21:
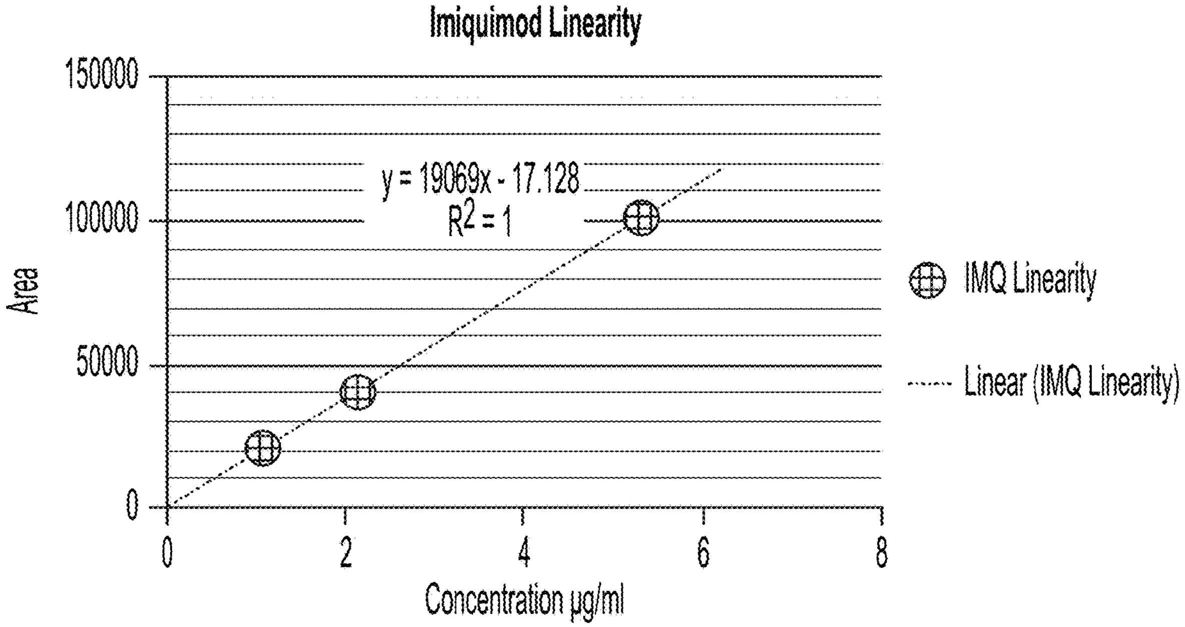
FIG. 21 depicts the Calibration Curve for Imiquimod.

The solubility of imiquimod and the imiquimod-ferulic acid cocrystal in water was evaluated. Each sample (Imiquimod, IMQ-Fe, or Ferulic Acid) was dissolved in water. Imiquimod was assayed using a reverse phase chromatographic method utilizing a Waters UPLC. The amount of imiquimod in samples of aqueous solutions of imiquimod was assayed by comparing to external standards. In the same sequence a ferulic acid standard was also run that allowed for independent calculation of ferulic acid content in cocrystal samples. The calibration curve for Imiquimod is shown in FIG. 21.

TABLE 2

Aqueous Solubility of Imiquimod, Ferulic Acid and IMQ-Fe

| Sample in water | Calculated Sample Concentration (mg/ml) | Calculated Sample Concentration (μg/ml) | Comment |
|---|---|---|---|
| Imiquimod | 0.0022 | 2.2 | Imiquimod |
| IMQ-Fe | IMQ 0.0939 | 93.9 | Imiquimod |
| | FA 0.1141 | 114.1 | Ferulic acid |
| Ferulic Acid | 0.8155 | 815.5 | Ferulic acid |

In addition to solubility, the pH of Imiquimod and IMQ-Fe were evaluated using a pH probe. The results are shown in the table below. The pH of Imiquimod was found to be 7.10 and the pH of IMQ-Fe was found to be 5.64.

TABLE 3

Aqueous Solubility of Imiquimod/Ferulic Acid Cocrystal

| Sample | Component | Concentration (unheated, mg/ml) | Concentration (heated for 1 hr @ 60 C., mg/ml) | pH |
|---|---|---|---|---|
| Imiquimod | IMQ | 0.002 | 0.002 | 7.10 |
| IMQ-Fe | IMQ | 0.049 (40.4%) | 0.094 (44.3%) | 5.64 |

Imiquimod is practically insoluble in water and sparingly soluble in other common organic solvents. The IMQ-Fe Cocrystal of the invention has significantly improved solubility, compared to imiquimod. The IMQ-Fe sample at equilibrium maximum aqueous solubility conditions demonstrates an enhanced solubility of approximately 40 times compared to the imiquimod sample.

In addition, the cocrystal IMQ-Fe was found to be stable at 40° C. 75% RH for at least a week.

Example 10: Summary of Cocrystal Evaluation

TABLE 4

| Cocrystal | PXRD (Novel Phase) | DSC | TGA | Comments |
|---|---|---|---|---|
| IMQ-Ci | ✓ 5.8, 23.4 | Unique melting point 121.1 & 205.5 | 5.0% weight loss at 120° C. | Appears to be a hydrate |
| IMQ-Ac | ✓ 6.7, 9.0 | Complex endotherms 72.5 & 96.1 | Two weight losses observed | Complex system |
| IMQ-Tar | ✓ 8.5, 26.1 | No melting peak observed up to 200° C. | 5.2% weight loss at 170° C. | Appears to be a hydrate |
| IMQ-Fe | ✓ 13.3, 28.1 | Unique melting point 226.4 | Negligible weight loss (~1%) up to 180° C.) | Appears to be anhydrous |
| IMQ coumarate | ✓ 9.0, 25.5 | Unique melting point 134.1 & 219.2 | 4.6% water at 150° C. | Appears to be a hydrate |

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

The invention claimed is:

1. A method of inhibiting viral replication in a subject in need thereof comprising administering to the subject a therapeutically effective amount of an active pharmaceutical ingredient selected from the group consisting of: IMQ-Fe, IMQ-Ac, IMQ-Ci, IMQ-Co, and IMQ-Tar.

2. The method of claim 1, wherein the subject is infected with a virus selected from the group consisting of influenza A virus, RSV, varicella-zoster virus, HSV, HIV/AIDS, HPV, MERS-CoV, Zika virus, Dengue virus, and MMR virus, or SARS-CoV-2.

3. The method of claim 2, wherein the subject has been infected with RSV.

4. A method of treating Long COVID in a subject in need thereof, comprising administering to the subject a therapeutically effective amount of an active pharmaceutical ingredient selected from the group consisting of IMQ-Fe, IMQ-Ac, IMQ-Ci, IMQ-Co, and/or IMQ-Tar.

5. The method of claim 2, wherein the active pharmaceutical ingredient is administered topically.

6. The method of claim 2, wherein the active pharmaceutical ingredient is administered to the nasopharyngeal area of the subject by spraying a composition comprising the active pharmaceutical ingredient into the nasal passage.

7. The method of claim 6, wherein the dose administered is 50 μl spray containing 25 μg of IMQ-Fe.

8. The method of claim 2, wherein the method further comprises administering ferulic acid to the subject.

9. A sprayable liquid composition in a spray bottle, the composition comprising an active pharmaceutical ingredient selected from the group consisting of: IMQ-Fe, IMQ-Ac, IMQ-Ci, IMQ-Co, and IMQ-Tar, and a pharmaceutically acceptable excipient.

10. The composition of claim 9, wherein the composition is a nasal spray.

11. The method of claim 4, wherein the active pharmaceutical ingredient is administered topically.

12. The method of claim 4, wherein the active pharmaceutical ingredient is administered to the nasopharyngeal area of the subject by spraying a composition comprising the active pharmaceutical ingredient into the nasal passage.

13. The method of claim 12, wherein the dose administered is 50 μl spray containing 25 μg of IMQ-Fe.

14. The method of claim 4, wherein the method further comprises administering ferulic acid to the subject.

* * * * *